US005468485A

United States Patent [19]

Curtiss, III

[11] Patent Number: 5,468,485
[45] Date of Patent: * Nov. 21, 1995

[54] AVIRULENT MICROBES AND USES THEREFOR

[75] Inventor: Roy Curtiss, III, St. Louis, Mo.

[73] Assignee: Washington University, St. Louis, Mo.

[ * ] Notice: The portion of the term of this patent subsequent to Mar. 15, 2011, has been disclaimed.

[21] Appl. No.: 20,259

[22] Filed: Feb. 18, 1993

Related U.S. Application Data

[63] Continuation of Ser. No. 332,285, Mar. 31, 1989, abandoned, which is a continuation-in-part of Ser. No. 200,934, Jun. 1, 1988, abandoned, which is a continuation-in-part of Ser. No. 58,360, Jun. 4, 1987, abandoned.

[51] Int. Cl.[6] .......................... A61K 39/00; A61K 39/02; C12N 1/21; C12N 15/00

[52] U.S. Cl. .................................... 424/184.1; 424/200.1; 424/93.1; 424/93.2; 435/69.1; 435/71.1; 435/172.1; 435/252.3; 435/252.33; 435/252.8

[58] Field of Search ............................ 424/88, 92, 184.1, 424/200.1, 241.1, 278.1, 93.1, 93.2; 435/253, 252.3, 252.33, 320.1, 69.1, 69.3, 172.1, 252.3, 252.33, 252.8

[56] References Cited

U.S. PATENT DOCUMENTS 4,550,081 10/1985 Stocker .................................. 435/253

OTHER PUBLICATIONS

Nnalue et al, Inf. & Imm. 1987 vol 55, pp. 955–962, Tests of the Virluence & Live Vaccine Efficacy of Auxotrophic & galE Derivatives of *Salm. choleraesuis.*

Crosa et al J of Bact, vol. 15, 115:301–315, 1973 Molecular Relationships Among the Salmonelleae.

Alper et al J. of Bact 133:149–157.

Komeda et al Molec. Gen Genet 142:289–298, 1975, The Role of cAMP in Flagellation of *Salmonella typhimurium.*

Wang et al PNAS 78:4684–4688 1981 Molecular Cloning & Amplification of the Adenylate Cyclase Gene.

Garges et al Cell 41:745–751 1985, Sites of Allosteric Shift in the Structures of the Cyclic AMP Receptor Protein.

Curtiss, III, et al., *Infection and Immunity* (1987) 55(12):3035–3043.

Nnalue et al., *Microbial Pathogenesis* (1989) 7:299–310.

Curtiss, III, et al., *Immunological Investigations* (1989) 18(1–4): 583–596.

Nakamura et al., *Japan Journal of Veterinary Science* (1988) 50:606–713.

*Primary Examiner*—Hazel F. Sidberry
*Attorney, Agent, or Firm*—Rogers, Howell & Haferkamp

[57] ABSTRACT

This invention provides a vaccine for the immunization of a vertebrate or invertebrate comprising an avirulent derivative of *S. choleraesuis*. The derivatives being substantially incapable of producing functional adenylate cyclase and/or cyclic AMP receptor protein. The invention also provides a vaccine for the immunization of a vertebrate and invertebrate comprising a virulent derivative of a pathogenic microbe said derivative being substantially incapable of producing functional adenylate cyclase and/or cyclic AMP receptor protein while being capable of expressing a recombinant gene derived from a pathogen of said vertebrate to produce an antigen capable of inducing an immune response in said vertebrate against said pathogen.

6 Claims, 8 Drawing Sheets

AVIRULENT MICROBES AND USES THEREFOR

REFERENCE TO GOVERNMENT GRANT

This invention was made with government support under Grant Numbers DE 06669 and AI 24533. The government has certain rights in this invention.

CROSS-REFERENCE TO RELATED APPLICATION

This is a continuation of application Ser. No. 07/332,285 filed on Mar. 31, 1989 now abandoned, which is a continuation-in-part of U.S. application Ser. No. 200,934, filed Jun. 1, 1988, abandoned which is a continuation-in-part of U.S. application Ser. No. 058,360, filed Jun. 4, 1987, now abandoned, which applications are hereby incorporated herein by reference.

FIELD OF THE INVENTION

This invention relates to avirulent microbes, their method of preparation, and their use in vaccines.

BACKGROUND OF THE INVENTION

Salmonellosis of swine is one of the most economically important of the enteric and septicemic diseases affecting young pigs, and has been described as a significant health problem in swine. Although many serotypes of Salmonella have been isolated from pigs, *S. choleraesuis* var. *kunzendorf* and *S. typhimurium* are the two most frequently isolated serotypes associated with clinical salmonellosis in swine (Wilcock, 1986). *S. choleraesuis* is host-adapted to swine and is often the etiologic agent of fatal septicemic disease with little involvement of the intestinal tract. This *S. choleraesuis* reservoir in swine is a concern not only because of its disease-causing potential for pigs, but also because of its public health significance for humans.

The disease caused by *S. choleraesuis* manifests in many clinical signs. The organism is inherently invasive, and does not require the massive luminal proliferation required by *S. typhimurium*. Lesions and necrosis occur in the submucosa and lamina propria of the gut. Mortality is high, and the duration and severity of the disease is unpredictable.

Currently there is little information on vaccine use for control of swine salmonellosis. A rough variant of *S. choleraesuis* was used by H. W. Smith (1965) to demonstrate protection after challenge with virulent *S. choleraesuis*. However, the animals developed fever, sublethal disease, and became shedders of the bacteria. The Smith strain is commercially available in Europe as Suscovax™, which is manufactured and distributed by Wellcome Laboratories. Hanna et al (1979) reported use of Smith's life attenuated *S. choleraesuis* vaccine by intramuscular route in pregnant sows. The piglets, after birth, had high titers of circulating maternally-derived antibodies, and resisted intranasal challenge. Although it has been reported that galE mutants of *S. typhimurium* are avirulent and immunogenic, in contrast, *S. choleraesuis* strains with galE mutations remain as virulent in mice as the wild-type gal$^+$ parent. *S. choleraesuis* auxotrophs with requirements for aromatic amino acids due to an aroA mutation have reduced virulence in mice, but were unable, even after three immunizing doses, to induce protective immunity. At present, the only *S. choleraesuis* vaccine licensed for use in the United States of America is a killed bacterial bactrin, which is not particularly effective in inducing protective immunity.

In general, previously used vaccines against infectious diseases have generally comprised (I) specific components purified from the etiologic agents, including intact antigens, fragments thereof, or synthetic analogs of naturally occurring antigens or epitopes, (II) antiidiotypic antibodies, (III) the whole killed etiologic agent, or (IV) an avirulent derivative of the etiologic agent as a live vaccine. Numerous vaccines of these types exist, of which the following are selected examples:

U.S. Pat. No. 4,250,262 discloses methods for recovering the enzyme glucosyltransferase from *Streptococcus mutans* and the use of this purified enzyme in local immunization against dental caries, a Type I vaccine. Details for culturing the bacteria, purifying the enzyme, and using the enzyme to stimulate IgA antibody in saliva are presented for serotype a, c or g of *S. mutans*. Other examples of vaccines from purified specific components of bacteria are found in U.S. Pat. Nos. 4,203,971 and 3,239,749, which disclose a vaccine useful against infection by *Neisseria gonorrhoeae* which consists of a glycoprotein from the outer coat material of gonococci. Injection of the glycoprotein stimulates a bactericidal antibody.

The use of dead *S. mutans* cells to immunize against tooth decay via administering in the mouth, which is disclosed in U.S. Pat. No. 3,931,398, is an example of a Type III vaccine. The inventors recognized that immunoglobulin A (IgA) antibodies were the antibodies being produced and that they resulted in a decrease in plaque formation.

A live bacterial vaccine (Type IV) which contains selected strains of *Escherichia coli* bacteria is disclosed in U.S. Pat. No. 3,975,517. The bacteria were treated with dilute formalin to attenuate or partially inactivate them before injection into the mammary gland of a sow. Antibody thereby produced was later found in the milk and protected newborn swine against *E. coli* infections. The formalin treatment that caused the *E. coli* inactivation was only a temporary attenuation of the bacteria and care had to be taken to prevent bacterial recovery before injection. Such recovery would have resulted in serious infection rather than protection.

It has been possible to develop avirulent strains by the introduction of mutations into said strains which results in the strains being substantially incapable of survival in a host. These strains can be said to be genetically attenuated. For ease of description the principles of genetic attenuation will be illustrated by reference to the Salmonella system, however, the principles are broadly applicable as will be discussed below.

*Salmonella typhimurium*, *S. typhi* and other Salmonella species with invasive properties enter deep tissues after oral ingestion by attaching to, invading and proliferating in the cells of the gut-associated lymphoid tissue (GALT; Peyer's Patches) (Carter and Collins, *J. Exp. Med.* 139:1189–1203, (1974)). Since Salmonella-mediated delivery of an antigen to the GALT elicits a generalized secretory immune response as well as humoral and cellular immune responses, avirulent Salmonella mutants that have lost the ability to cause disease without impairment in their ability to attach to and invade the GALT are likely to serve as effective vectors to deliver foreign antigens, such as colonization or virulence antigens, to the GALT and to induce protective immunity against the pathogen from which such antigens were derived. The construction of avirulent Salmonella vaccine strains that express antigens from other microorganisms has been accomplished via classical gene transfer procedures (Formal et al., *Infect. Immun.* 34:746– 750, (1981)) as well as by using recombinant DNA technologies. In the latter case, avirulent Salmonella strains have been constructed expressing genes from organisms that normally exchange genetic information with Salmonella (Stevenson and Manning, *FEMS Microbiol. Lett.* 28:317–321 (1985); Clements et al., *Infect. Imm.* 53:685– 692, (1986)), as well as from microorganisms that are unable to transfer genetic information to Salmonella by classical means of gene transmission (Curtiss, *J. Dent. Res.* 65:1039–1045 (1986)). Such bivalent avirulent Salmonella strains have been shown to elicit antibodies and in one instance a cellular immune response (Brown et al., *J. Infect. Dis.* 155:86–92 (1987)) to the expressed antigen, but data pertaining to induction of protective immunity against the pathogen supplying the colonization or virulence antigen is still scant.

Bacon et al, (*Brit. J. Exp. Pathol.* 32:85–96, (1951)) were first to investigate the avirulence of auxotrophic mutants of *S. typhi*. They noted that mutants with requirements for purines, p-aminobenzoic acid, and aspartate had reduced virulence for mice. Germanier and Furer, (*Infect. Immun.* 4:663–673, (1971)) first investigated use of galE mutants of *S. typhimurim* for avirulence and immunogenicity in mice and then proposed use of the *S. typhi* galE mutant Ty21a as a vaccine against typhoid fever in humans (*J. Infect. Dis* 131:553–558 (1975)). Stocker (U.S. Pat. No. 4,550,081) employed transposon mutagenesis with Tn10 followed by selection for fusaric acid resistance that leads to deletional loss of Tn10 and adjacent DNA sequences to yield deletion mutations unable to revert, a problem that was apparent in the mutants used by Bacon et al. Stocker initially isolated aroA deletion (delta) mutants impaired in the ability to synthesize the aromatic amino acid family of compounds, including p-aminobenzoic acid needed for folate biosynthesis and dihydroxybenzoic acid, a precursor to enterochelin, and more recently combined the delta-aroA mutation with a deletion mutation abolishing adenine biosynthesis. Tn10-induced and fusaric acid resistance-generated delta-asd mutations that impose a requirement for diaminopimelic acid have been employed to render *S. typhimurium* avirulent without impairing its ability to induce a generalized secretory immune response. Since many Salmonella possess a plasmid that contributes to virulence, plasmid-cured derivatives have been investigated and proposed for use as live vaccines (Nakamura et al, *Infect. Immun.* 50:586–587 (1985)).

Although each of the above described means for rendering Salmonella avirulent without impairing immunogenicity has merit, each has problems. galE mutants are difficult to grow to maintain immunogenicity, since they are galactose-sensitive but must be grown in the presence of galactose to produce normal LPS which, however, selectively leads to galactose-resistant variants that are non-immunogenic. Although delta-aroA mutants abolish the synthesis of both enterochelin and folic acid, the necessity of enterochelin for *S. typhimurium* virulence has been called into question by the extensive results of Benjamin et al. (*Infect. Immun.* 50:392–97 (1985)) that demonstrate that any and all mutations that interfere with *S. typhimurium*'s ability to chelate and transport iron are without significant effect on virulence. Therefore, the avirulence of delta-aroA mutants is most likely solely due to the inability to synthesize p-aminobenzoic acid (pABA) and therefore folic acid. Since Bacon et al. (supra) observed that administering p-aminobenzoic acid in the diet of mice infected with mutants unable to synthesize pABA led to wild-type levels of virulence, one must be concerned with phenotypic reversal of avirulence in vaccine strains due to dietary consumption of metabolites whose synthesis is blocked in the avirulent mutants. The delta-asd mutants, although not having some of these other difficulties, rapidly die following oral feeding and invasion of the GALT, and are thus only effective at eliciting a generalized mucosal immunity and are ineffective in inducing humoral and cellular immunity.

This invention addresses many of the deficiencies of the prior art vaccines by employing transposon-induced mutants in which the impairment leading to avirulence cannot be repaired by diet or by anything the animal host could supply. These deletions could, of course, be introduced by recombinant DNA techniques.

BRIEF DESCRIPTION OF THE INVENTION

The strains provided herein are directly and indirectly suitable for the production of commercial vaccines to prevent diseases caused by *S. choleraesuis*, and other enteric bacteria with which antibodies to *S. choleraesuis* cross react. These strains are also useful as carrier microorganisms for the production of expression products encoded on recombinant genes in the bacterial cells.

Accordingly, one embodiment of the invention is a vaccine for the immunization of an individual comprising an avirulent derivative of pathogenic *S. Choleraesuis*, said derivative being substantially incapable of producing functional adenylate cyclase due to a mutation in a cya gene.

Another embodiment of the invention is a method for stimulating the immune system to respond to an immunogenic antigen of *S. choleraesuis* comprising administering to said individual an avirulent derivative of pathogenic *S. choleraesuis*, said derivative being substantially incapable of producing functional adenylate cyclase due to a mutation in a cya gene.

Still another embodiment of the invention is a method for stimulating the immune system to respond to an immunogenic antigen of a pathogen comprising administering to said individual an avirulent derivative of pathogenic *S. choleraesuis*, said derivative being substantially incapable of producing functional adenylate cyclase and cyclic AMP protein and being capable of expressing a recombinant gene encoding the immunogenic antigen, to produce an antigen capable of inducing an immune response in said vertebrate against said pathogen.

Another embodiment of the invention is an isolated avirulent strain of *S. choleraesuis* which is substantially incapable of producing functional adenylate cyclase.

Still another embodiment of the invention is a vaccine for the immunization of an individual comprising an avirulent derivative of pathogenic *S. Choleraesuis*, said derivative being substantially incapable of producing functional cyclic AMP receptor protein (crp) due to a mutation in a crp gene.

Yet another embodiment of the invention is a method for stimulating the immune system to respond to an immunogenic antigen of *S. choleraesuis* comprising administering to said individual an avirulent derivative of pathogenic *S. choleraesuis*, said derivative being substantially incapable of producing functional crp due to a mutation in a crp gene.

Another embodiment of the invention is a method for stimulating the immune system to respond to an immunogenic antigen of a pathogen comprising administering to said individual an avirulent derivative of pathogenic *S. choleraesuis*, said derivative being substantially incapable of producing functional crp and being capable of expressing a recombinant gene encoding the immunogenic antigen, to produce an antigen capable of inducing an immune response in said vertebrate against said pathogen.

Yet another embodiment of the invention is isolated avirulent strain of S. choleraesuis which is substantially incapable of producing functional Crp due to a mutation in a crp gene.

Still another embodiment of the invention is a vaccine for the immunization of an individual comprising an avirulent derivative of pathogenic S. choleraesuis, said derivative being substantially incapable of producing functional adenylate cyclase and cyclic AMP receptor protein (Crp) due to a mutation in a cya and crp gene.

Yet another embodiment of the invention is a method for stimulating the immune system to respond to an immunogenic antigen of S. choleraesuis comprising administering to said individual an avirulent derivative of pathogenic S. choleraesuis, said derivative being substantially incapable of producing functional adenylate cyclase or Crp due to a mutation in a cya gene and a crp gene.

Another embodiment of the invention is a method for stimulating the immune system to respond to an immunogenic antigen of a pathogen comprising administering to said individual an avirulent derivative of pathogenic S. choleraesuis, said derivative being substantially incapable of producing functional adenylate cyclase and Crp and being capable of expressing a recombinant gene encoding the immunogenic antigen, to produce an antigen capable of inducing an immune response in said vertebrate against said pathogen.

Still another embodiment of the invention is an isolated avirulent strain of S. choleraesuis which is substantially incapable of producing functional adenylate cyclase and Crp due to a mutation in a cya gene and a crp gene.

Another embodiment of the invention is a strain selected from the group of strains ATCC 56347, ATCC 53648, ATCC 67923, ATCC 53885, ATCC 67922, and mutants thereof, and derivatives thereof.

DETAILED DESCRIPTION OF THE FIGURES

Figure 1:
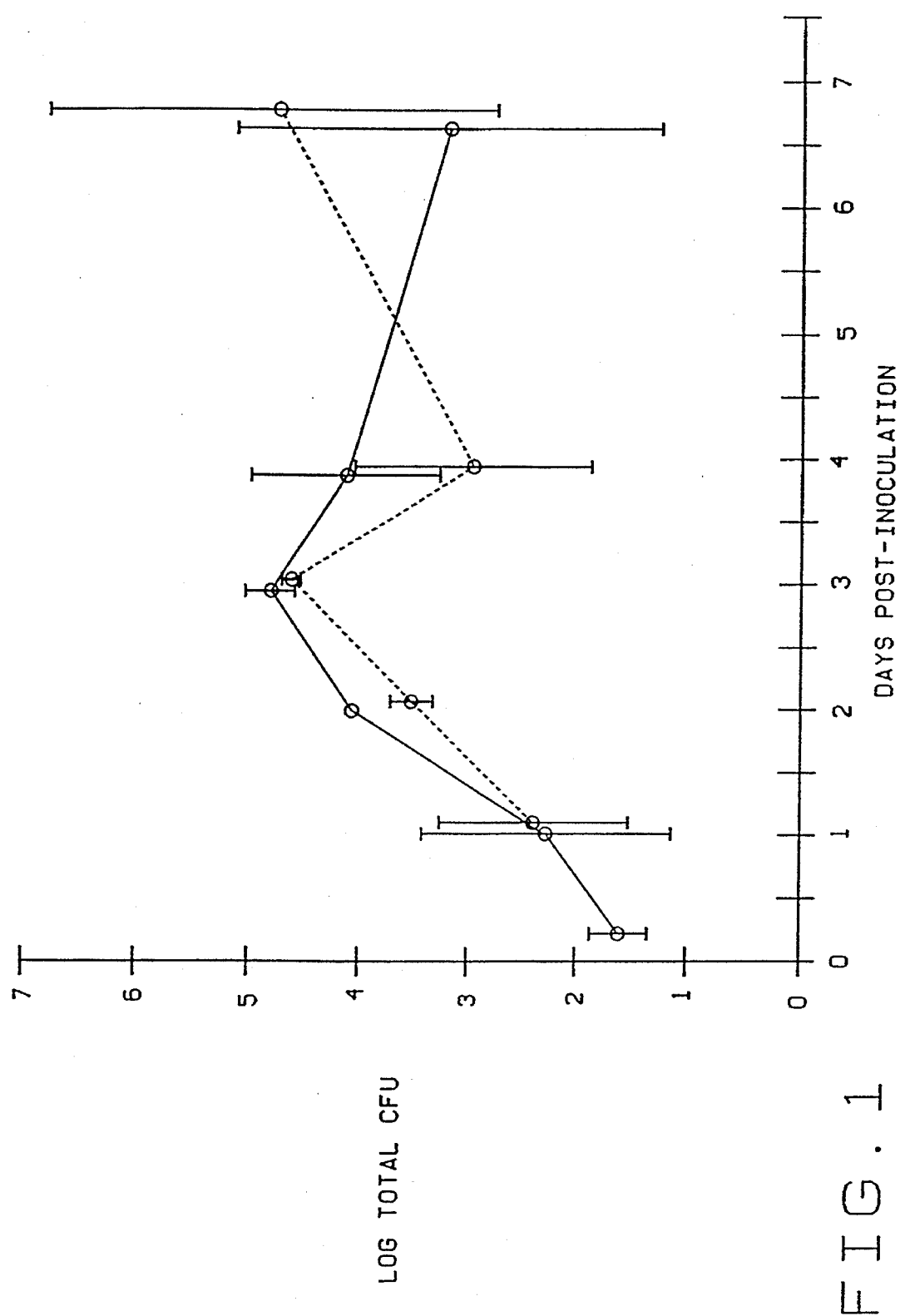

FIG. 1 illustrates the recovery of S. typhimurium delta-cya delta-crp Chi4064 (open circle) and wild-type Chi3456 (open circle) from Peyer's patches (i.e., GALT) at specified time after peroral inoculation with $7.4 \times 10^8$ cfu of Chi4064 and $4.0 \times 10^8$ cfu of Chi3456. The vertical bars denote the standard deviations.

Figure 2:
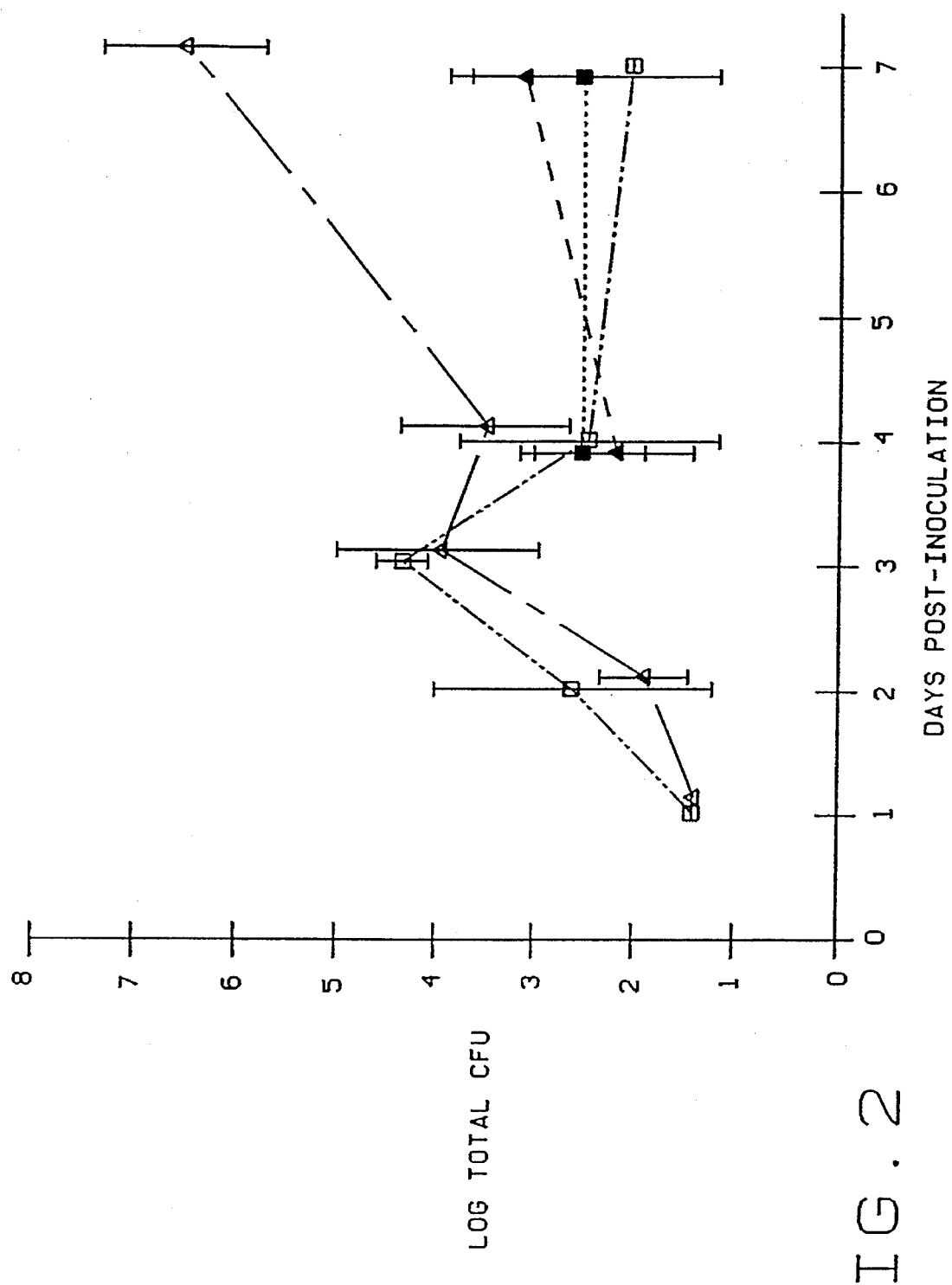

FIG. 2 illustrates the recovery of S. typhimurium delta-cya delta-crp (closed square, closed triangle) and wild-type Chi3456 (open square, open triangle) from mesenteric lymph nodes (closed square, open square) and spleen (open triangle, open triangle) at specified times after peroral inoculation with $7.4 \times 10^8$ cfu of Chi4064 and $4.0 \times 10^8$ cfu of Chi3456. The vertical bars denote the standard deviations.

Figure 3:
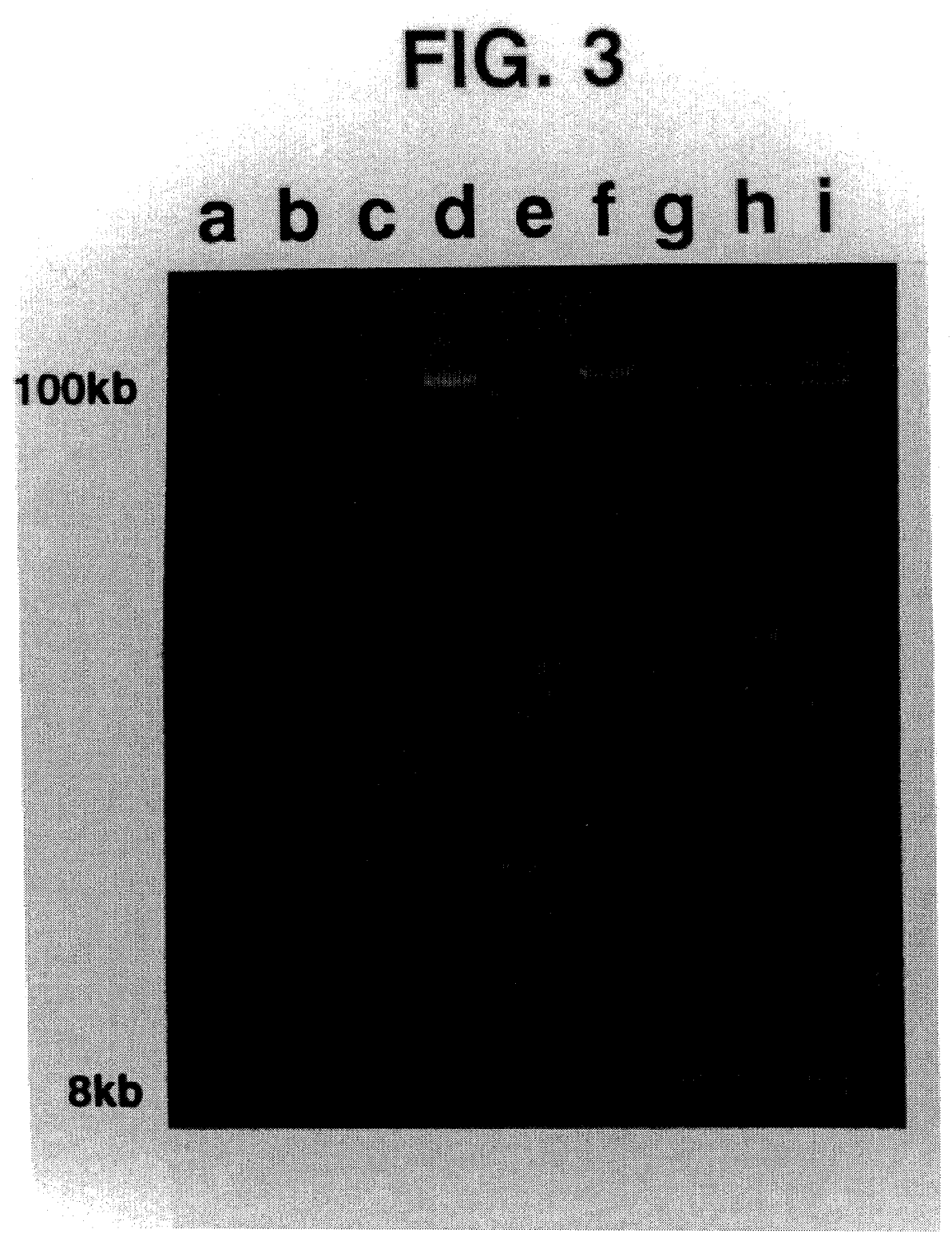

FIG. 3 illustrates the plasmid content of certain S. typhimurium strains. Plasmid DNA was extracted by the method of Birnboim (Methods, Enzmol. 100:243–255, 1983), resolved in a 0.5% (wt/vol) agarose gel, and stained with ethidium bromide. Chi3344 and Chi3337 lysates were extracted with phenol/chloroform/ether and not subjected to density gradient centrifugation. Strain (100 kb plasmid) in lanes: a, Chi3000(pStLT100); b, Chi3344(–); c, Chi3347(pStLT101); d, Chi3306(pStSR100); e, Chi3337(–); f, Chi3338(pStSR101); g, Chi3339(pStSL100, 90 kb, 8 kb); h, Chi3340(90 kb, 8 kb); i, Chi3351(pStSR101). Marker plasmids were R1drd (100 kb) and dimeric pACYC184 (8 kb) (not shown).

Figure 4:
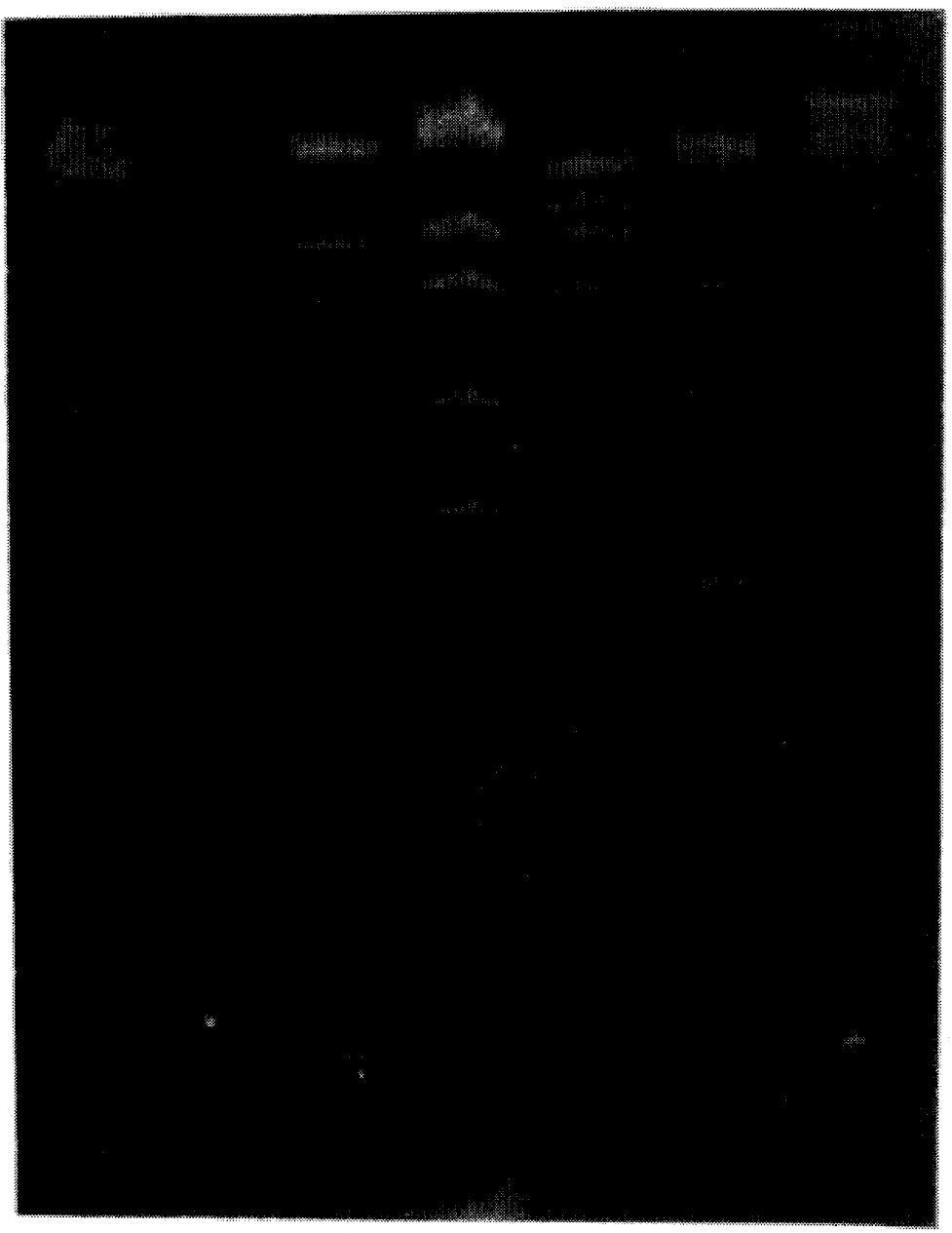

FIG. 4 illustrates the restriction enzyme digestion profiles of 100 kb plasmids. Plasmid DNA was digested with HindIII, resolved in a 0.6% (wt/vol) agarose gel, and stained with ethidium bromide. Lane a contains phage lambda-DNA digested with HindIII. The following strains (and corresponding plasmid content) are shown in lanes: b, Chi3000(pStLT100); c, Chi3306(pStSR100); d, Chi3338(pStSR101); e, 3339(pStSL100, 90 kb, 8 kb); and f, Chi3340 (90 kb, 8 kb).

Figure 5A:
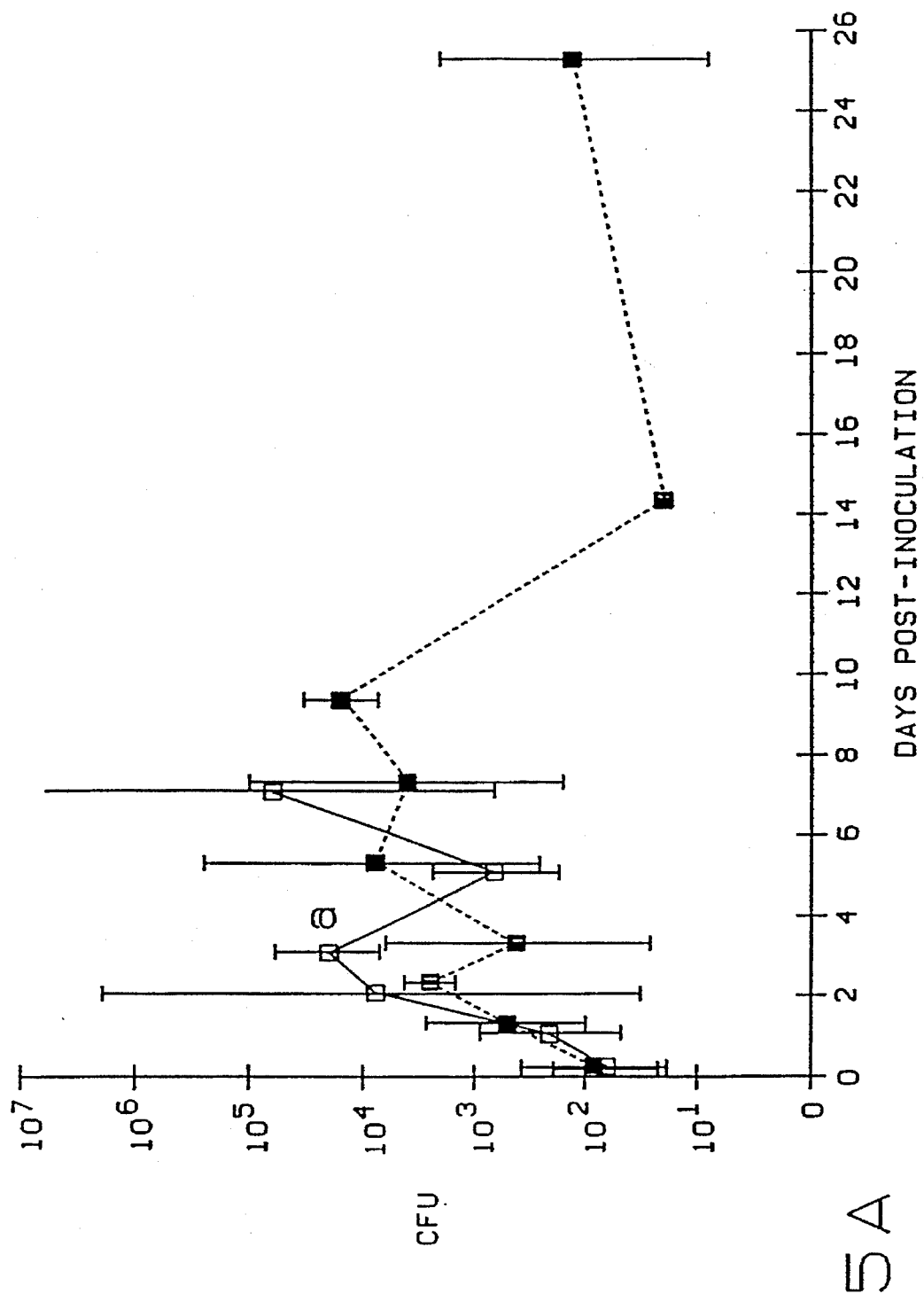
Figure 5B:
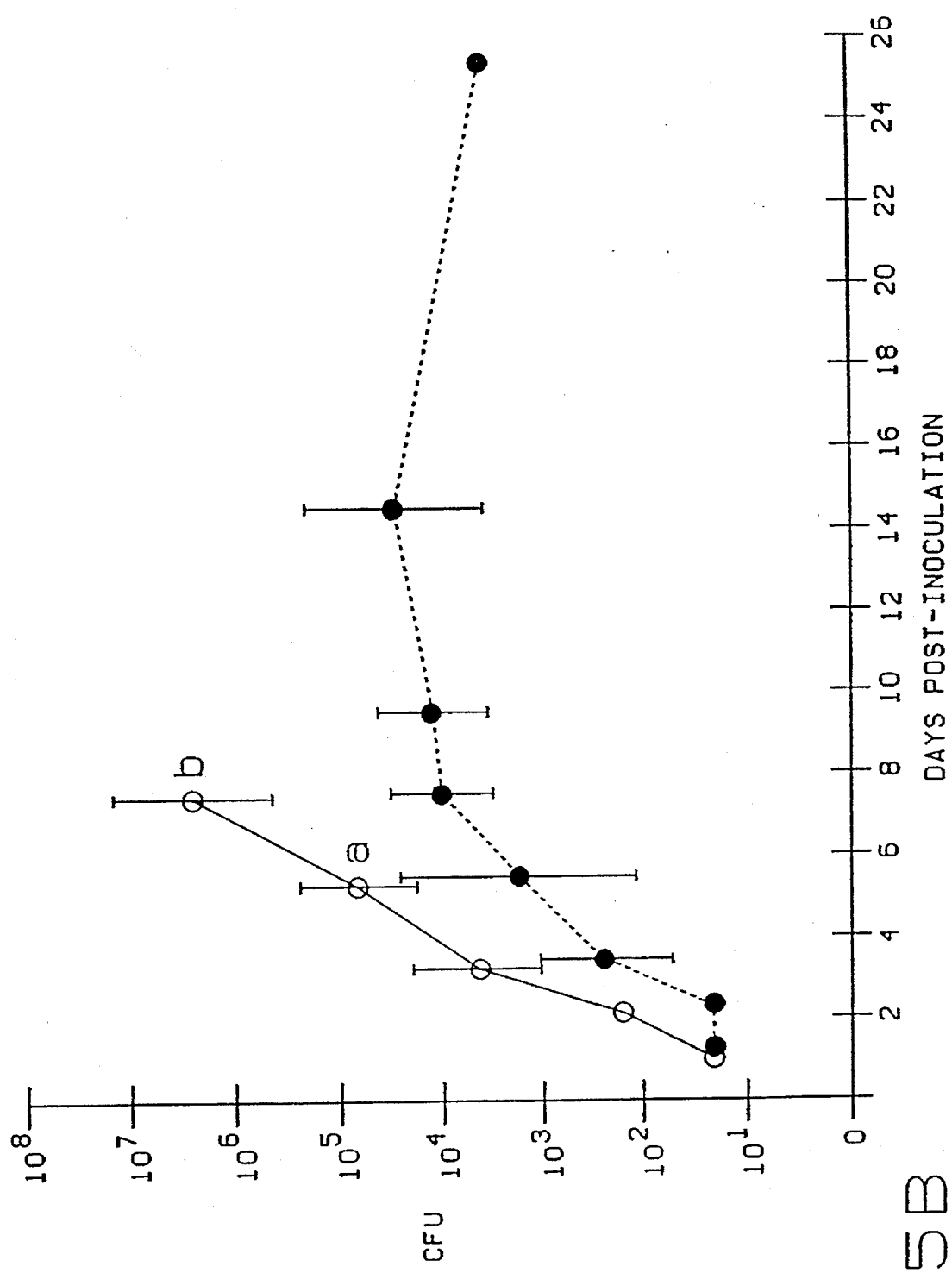

FIG. 5 illustrates the total CFU in (A) Peyer's patches and (B) spleens after p.o. inoculation of mice with S. typhimurium SR-11. Chi3306 (open circle, open square), Chi3337 (open circle, open square). Geometric mean ±SD, n=2 to 7 mice. P values in 1-tailed Student's t test for CFU Chi3306 greater than Chi3337: $^a<0.0125$, $^b<0.0005$.

Figure 6:
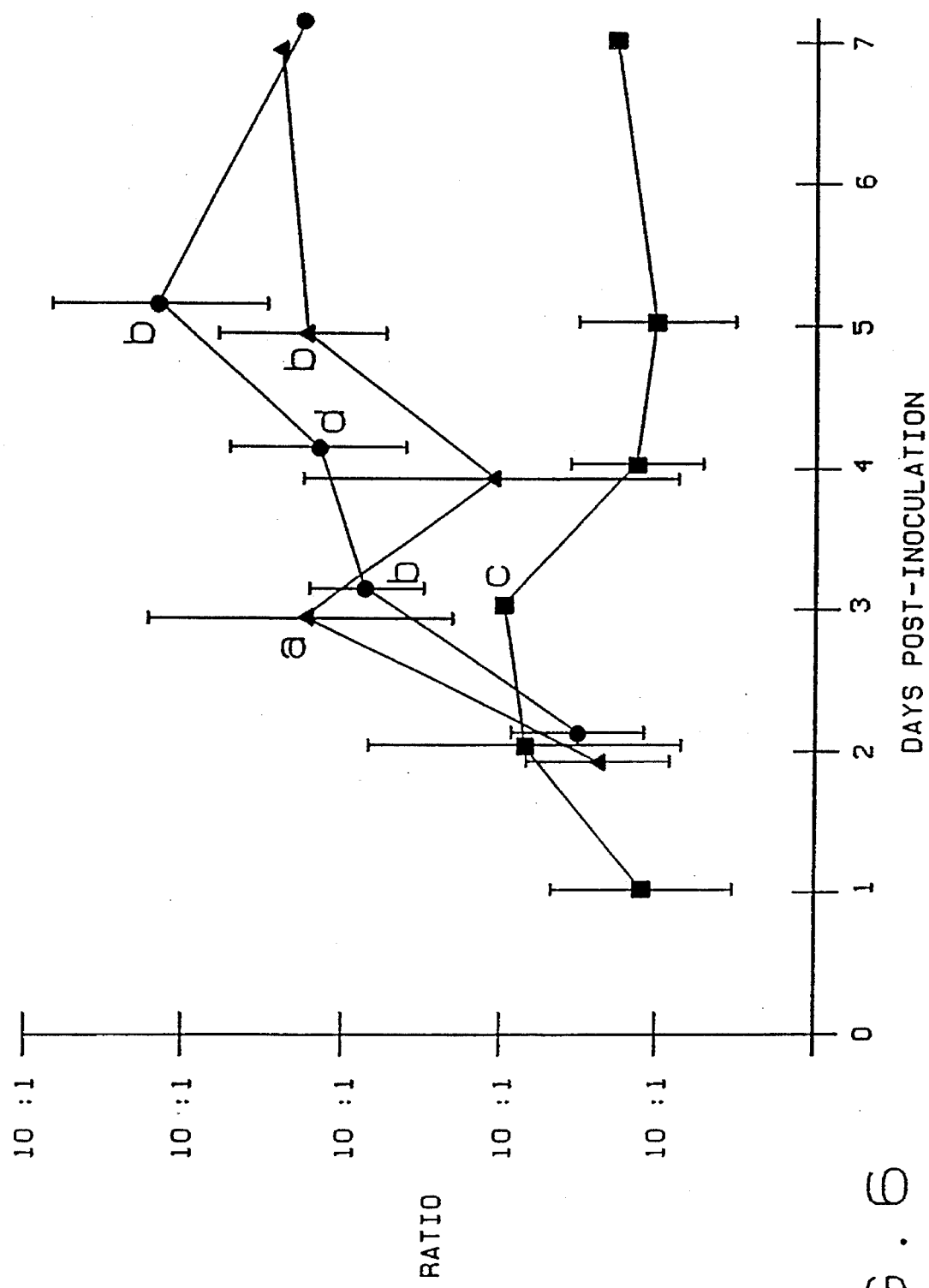

FIG. 6 illustrates the results of a mixed p.o. infection of mice with wild-type and 100 kb plasmid-cured Sr-11. Geometric mean±SD of ratios of wild-type Chi3456 to cured Chi3337 recovered from Peyer's patches (open circle), mesenteric lymph nodes (open triangle), and spleens (open square). n=3 to 7 mice, n=1 for 7 days post-inoculation. P values in 1-tailed Student's t test for geometric mean of ratio grater than 1: $^a<0.05$, $^b<0.0125$, $^c<0.0025$, $^d<0.0005$.

Ratio of spleens was greater than ratio of Peyer's patches at 3 days (P<0.0125), 4 days (P<0.0005), and 5 days (P<0.025) post-infection. Ratio of mesenteric lymph nodes was greater than ratio of Peyer's patches at 3 days (P<0.05) and 5 days (P<0.005) post-infection.

Figure 7:
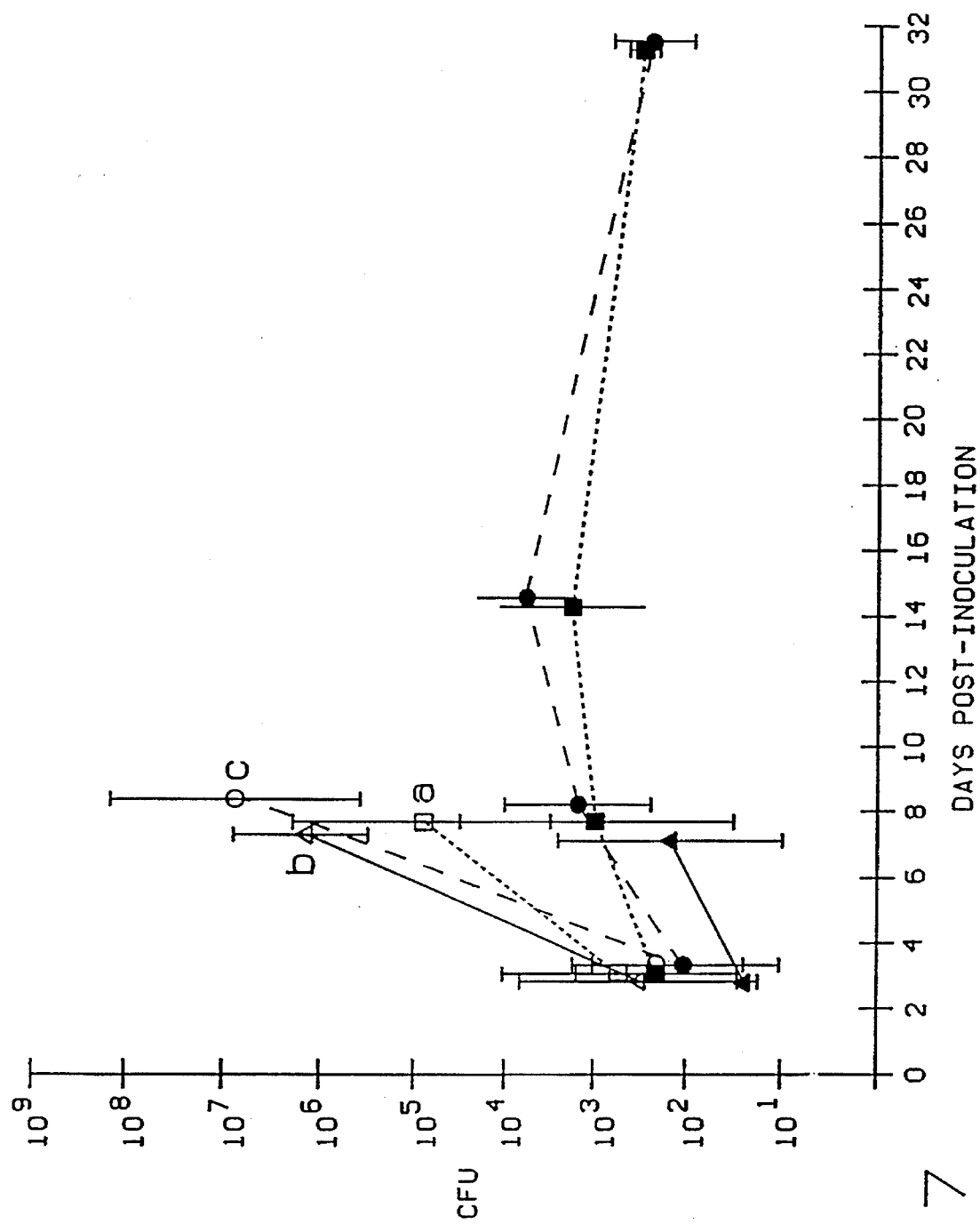

FIG. 7 illustrates the CFU in mouse tissues after p.o. inoculation of mice with SL1344. Chi3339 (open symbols), Chi3340 (filled symbols). Peyer's patches (open square, closed square), mesenteric lymph nodes (triangle, closed triganle), spleens (open circle, closed circle). Geometric mean±SD, n=2 to 7 mice. P values in a 1-tailed Student's t test for CFU Chi3339 greater than Chi3340: $^a<0.025$, $^b<0.0125$, $^c<0.0005$.

DETAILED DESCRIPTION OF THE INVENTION

This invention is predicated on the discovery that certain mutations can render a microbe avirulent without substantially affecting its immunogenicity. More specifically, this invention relates to microbial vaccines in which the microbe carries the deletion (open triangle) mutations delta-cya and delta-crp eliminating the ability to synthesize adenylate cyclase (ATP pyrophosphate lyase (cyclizing) EC 4.6.1.1) and the cyclic AMP receptor protein (CRP), respectively.

Cyclic-3'5'-AMP (cAMP) and the cyclic AMP receptor protein are necessary for the transcription of a large number of genes and operons concerned with the transport and breakdown of a large number of catabolites. Evidence has been provided that shows that systems used for transporting fuel/carbon sources are all under positive control by cAMP, as are several amino acid permeases. In addition to its very important role in catabolism, the cAMP concentration in cells also influences lysogenization by temperate phages, synthesis of fimbriae, synthesis of flagella and synthesis of at least one outer membrane protein. Although cAMP is present in mammalian cells, the concentrations present in macrophages and other cells in which Salmonella can invade and multiply are below the concentration of 0.1 to 1.0 mM cAMP necessary to allow delta-cya mutants to exhibit a wild-type phenotype in vitro. Furthermore, the inclusion of the delta-crp mutation would essentially abolish any benefit that could accrue from uptake of cAMP in vitro by such delta-cya mutants.

Once rendered avirulent by the introduction of the delta-cya delta-crp mutations, the microbes can serve as the immunogenic component of a vaccine to induce immunity against the microbe. Thus, the use of any microbe possessing the genes for adenylate cyclase and cAMP receptor proteins are contemplated by this invention, including but not limited to Salmonella, *E. coli-S. typhimurium* hybrids, Shigella, Erwinia, Yersinia, Pasteurella, Legionella or Brucella. Preferred microbes are members of the genus Salmonella such as *S. typhimurium, S. typhi, S. paratyphi, S. gallinarum, S. enteritidis, S. choleraesuis, S. arizona,* or *S. dublin.*

In another embodiment of the invention, the avirulent derivative of a pathogenic microbe also referred to herein as a carrier bacteria can be used to deliver selected antigens to the GALT, for example to the Peyer's patches of the ileum. Some genera of bacteria, such as Salmonella, are known to home to the Peyer's patches (Carter, P. B. and F. M. Collins, *J. Exp. Med.* 139:1189 (1974)). *S. typhimurium-E. coli* hybrids have also been shown to colonize Peyer's patches in mice (Hohmann, A. W., et al., *Infect. and immun.* 22:763 (1978)). If these carrier bacteria contain and express a recombinant gene from a pathogenic organism, antibodies against the antigenic gene product produced from the pathogen will be induced. With the advent of recombinant DNA techniques, it now becomes possible to develop totally unique vaccines in which specific antigens are produced, not by the etiologic agent, but by another host strain of bacteria capable of expressing the gene for that antigen. It is also possible, when antigens might cross-react with an antigen of the mammalian host and thus potentiate the induction of autoimmunity, to use recombinant DNA techniques to alter the gene so that the affecting cross-reacting antigenic determinant is not produced. Thus, recombinant DNA techniques can be employed to develop vaccines that do not have any material capable of cross-reacting with vertebrate host antigens or capable of eliciting an autoimmune state.

It is apparent that the present invention has wide applicability to the development of effective vaccines against bacterial, fungal, parasite or viral disease agents where local immunity is important and might be a first line of defense. Some examples are vaccines for the control of pneumonic plague caused by *Yersinia pestis,* of gonorrhea caused by *Neisseria gonorrhoeae,* of syphilis caused by *Treponema pallidum,* and of venereal diseases as well as eye infections caused by *Chlamydia trachomatis.* Species of Streptococci from both group A and group B, such as those species that cause sore throat or heart disease, *Neisseria meningitidis, Mycoplasma pneumoniae, Hemophilus influenzae, Bordetella pertussis, Mycobacterium tuberculosis, Mycobacterium leprae, Bordetella avium, Escherichia coli, Streptococcus equi, Streptococcus pneumoniae, Brucella abortus, Pasteurella hemolytica, Vibrio cholera,* Shigella species, and *Legionella pneumophila* are additional examples of bacteria within the scope of this invention from which genes could be obtained. Viral vaccines, such as those produced against influenza viruses, are also encompassed by this invention. Viral vaccines can also be produced against other viruses, either DNA or RNA viruses, for example from the classes Papovavirus, Adenovirus, Herpesvirus, Poxvirus, Parvovirus, Reovirus, Picornavirus, Myxovirus, Paramyxovirus, or Retrovirus. Vaccines to protect against infection by pathogenic fungi, protozoa and parasites are also contemplated by this invention.

In a further embodiment, when the immunogenic component of the vaccine is an allergen of the host such a vaccine may be used in an exposure regimen designed to specifically desensitize an allergic host.

In one of its embodiments, the invention can be described as a vaccine for the immunization of a vertebrate animal or invertebrate comprising a live avirulent derivative of a pathogenic microbe said derivative being incapable of producing functional adenylate cyclase and cAMP receptor protein while being capable of expressing a recombinant gene derived from an organism that is a pathogen of or that produces an allergen of said animal.

In yet another embodiment the avirulent microbes of this invention may be used as vectors for the synthesis of various host proteins. Because the avirulent microbes of this invention are able to traverse a variety of immunocompetent structures including GALT, mesenteric lymph nodes and spleen after introduction into the host, such microbes may be used to target a variety of immunoregulatory products. Accordingly, one or more genes encoding immunoregulatory proteins or peptides may be recombinantly introduced into the avirulent microbes such that when the microbes taking up residence in the appropriate immunocompetent tissue are capable of expressing the recombinant product to suppress, augment or modify the immune response in the host. Examples of immunoregulatory molecules include but are not limited to: colony stimulating factors (macrophage, granulocyte, or mixed), macrophage chemotoxin, macrophage inhibition factor, leukocyte inhibitory factors, lymphotoxins, blastogenic factor, interferon, and interleukins.

Still another embodiment of the subject invention is the use of the avirulent microbes contemplated herein to deliver and produce pharmacologically active products that might stimulate or suppress various physiological functions (i.e., growth rate, blood pressure, etc.).

In an embodiment which contemplates all of the above, a subject of the invention is avirulent strains of *S. choleraesuis,* which carry mutations in the cya and/or crp genes.

Each of the terms in these embodiments of the invention is analyzed in the following discussion.

By vaccine is meant an agent used to stimulate the immune system of a living organism so that protection against future harm is provided. Immunization refers to the process of inducing a continuing high level of antibody and/or cellular immune response in which T-lymphocytes can either kill the pathogen and/or activate other cells (e.g., phagocytes) to do so in an organism, which is directed against a pathogen or antigen to which the organism has been previously exposed. Although the phrase "immune system" can encompass responses of unicellular organisms to the presence of foreign bodies, e.g., interferon production, in this application the phrase is restricted to the anatomical features and mechanisms by which a multi-cellular organism produces antibodies against an antigenic material which invades the cells of the organism or the extra-cellular fluid of the organism. The antibody so produced may belong to any of the immunological classes, such as immunoglobulins A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example, cellular and humoral immunity. Immune response to antigens is well studied and widely reported. A survey of immunology is given in Barrett, James, T., *Textbook of Immunology:* Fourth Edition, C. V. Mosby Co., St. Louis, Mo. (1983), the entirety of which is herein incorporated by reference.

A vertebrate is any member of the subphylum Vertebrata, a primary division of the phylum Chordata that includes the fishes, amphibians, reptiles, birds, and mammals, all of which are characterized by a segmented bony or cartilaginous spinal column. All vertebrates have a functional immune system and respond to antigens by producing antibodies. Thus, all vertebrates are capable of responding to vaccines. Although vaccines are most commonly given to mammals, such as humans or dogs (rabies vaccine), vaccines for commercially raised vertebrates of other classes, such as the fishes and birds if of the nature described herein, are within the scope of the present invention.

An invertebrate is any member of the Animal Kingdom, excluding the vertebrates. Such animals constitute the Division Invertebrata and have no backbone or spinal column. This classification includes all animals except fishes, amphibians, reptiles, birds and mammals. Many invertebrates are capable of illiciting a primitive immune response to antigenic stimulation and are susceptible to the same microorganisms which infect vertebrates and which are disclosed herein in accordance with this invention. Exemplary of such invertebrates are shellfish and molluses and other related animals. Although the use of vaccines in the protection of invertebrate animals has hitherto before not been well documented, one skilled in the art will recognize the applicability of the subject invention to said invertebrates by use of their primitive immune systems. For example, and in accordance with this invention, the susceptibility of shellfish to infection by Salmonella will allow the introduction of avirulent strains of Salmonella species and thereby provide potential for the primitive immune system to respond. Therefore, it is within the scope of this invention, the use of an avirulent derivative of a pathogenic microbe, that is capable of infecting an invertebrate, to stimulate a response from an immune system present in said invertebrate against a pathogen.

An "individual" treated with a vaccine of the invention is defined herein as including all vertebrates, for example, mammals, including domestic animals and humans, various species of birds, including domestic birds, particularly those of agricultural importance. In addition, mollusks and certain other invertebrates have a primitive immune system, and are included as an "individual".

In one embodiment of the invention is the use of an avirulent derivative of a pathogenic microbe that homes to the GALT or BALT as a carrier of the gene product which is used for stimulating antibody response against a pathogen or allergen. Avirulent does not mean that a microbe of that genus or species cannot ever function as a pathogen, but that the particular microbe being used is avirulent with respect to the particular animal being treated. The microbe may belong to a genus or even a species that is normally pathogenic but must belong to a strain that is avirulent. By pathogenic is meant capable of causing disease or impairing normal physiological functioning. Avirulent strains are incapable of inducing a full suite of symptoms of the disease that is normally associated with its virulent pathogenic counterpart. Microbes as used herein include bacteria, protozoa, and unicellular fungi.

Techniques for transferring genetic material from a first organism to a second organism which normally does not exchange genetic material with the first organism, have recently become widely available as the result of rapidly expanding recombinant DNA technology. In this application, genetic material that has been transferred from one organism into a second in such a manner that reproduction of the second organism gives rise to descendents containing the same genetic material is referred to as a recombinant gene. The term gene is being used here in its broadest sense to represent any biological unit of heredity. It is not necessary that the recombinant gene be a complete gene as present in the parent organism, which was capable of producing or regulating the production of a macromolecule, for example, a functioning polypeptide. It is only necessary that the gene be capable of serving as the template used as a guide in the production of an antigenic product. The product may be one that was not found in that exact form in the parent organism. For example, a functional gene coding for a polypeptide antigen comprising 100 amino acid residues may be transferred in part into a carrier microbe so that a peptide comprising only 75, or even 10, amino acid residues is produced by the cellular mechanism of the host cell. However, if this gene product is an antigen that will cause formation of antibodies against a similar antigen present in the parent organism, the gene is considered to be within the scope of the term gene as defined in the present invention. Alternatively, if the amino acid sequence of a particular antigen or fragment thereof is known, it is possible to chemically synthesize the DNA fragment or analog thereof by means of automated gene synthesizers or the like and introduce said DNA sequence into the appropriate expression vector. At the other end of the spectrum is a long section of DNA coding for several gene products, one or all of which can be antigenic. Thus, a gene as defined and claimed here is any unit of heredity capable of producing an antigen. The gene may be of chromosomal, plasmid, or viral origin.

In order for the gene to be effective in eliciting an immune response, the gene must be expressed. Expression of a gene means that the information inherent in the structure of the gene (the sequence of DNA bases) is transformed into a physical product in the form of an RNA molecule, polypeptide or other biological molecule by the biochemical mechanisms of the cell in which the gene is located. The biological molecule so produced is called the gene product. The term gene product as used here refers to any biological product or products produced as a result of the biochemical reactions that occur under the control of a gene. The gene product may be, for example, an RNA molecule, a peptide, or a product produced under the control of an enzyme or other molecule that is the initial product of the gene, i.e., a metabolic product. For example, a gene may first control the synthesis of an RNA molecule which is translated by the action of ribosomes into an enzyme which controls the formation of glycans in the environment external to the original cell in which the gene was found. The RNA molecule, the enzyme, and the glycan are all gene products as the term is used here. Any of these as well as many other types of gene products, such as glycoproteins and polysaccharides, will act as antigens if introduced into the immune system of an animal. Protein gene products, including glycoproteins and lipoproteins, are preferred gene products for use as antigens in vaccines.

In order for a vaccine to be effective in producing antibodies, the antigenic material must be released in such a way that the antibody-producing mechanism of the vaccinated animal can come into play. Therefore, the microbe carrier of the gene product must be introduced into the animal. In order to stimulate a preferred response of the GALT or BALT cells as discussed previously, introduction of the microbe or gene product directly into the gut or bronchus is preferred, such as by oral administration, gastric intubation or in the form of aerosols, although other methods of administering the vaccine, such as intravenous, intramuscular, subcutaneous injection or intramammary or intrapenial or vaginal administration, are possible.

When the avirulent microbe is used as a carrier microbe, and once the carrier microbe is present in the animal, the antigen needs to become available to the animal's immune system. This may be accomplished when the carrier microbe dies so that the antigen molecules are released. Of course, the use of "leaky" avirulent mutants that release the contents of the periplasm without lysis is also possible. Alternatively, a gene may be selected that controls the production of an antigen that will be made available by the carrier cell to the outside environment prior to the death of the cell. In this way, it is possible to use a viable microbe that will persist in the vaccinated animal, for example in its Peyer's patches, and continue to produce antigen, thereby continually inducing antibody formation. A preferred gene product under these circumstances is a product that is transferred through the cell membrane into the external environment or a product that becomes attached to or embedded in the external membrane so that all or part of the gene product is exposed to the environment. Typical of this latter type of gene product are antigens normally found on the surface of the organism against which protection is desired. If these antigens are transported to the cell surface in a normal manner, antibody formation against the antigens will be enhanced.

The use of pathogens to deliver antigens from other pathogens to the GALT or BALT would be inappropriate if it were not for the fact that such pathogens can be rendered avirulent while retaining ability to invade Peyer's patches or the BALT.

The organism from which the recombinant gene is derived may be any pathogen of the animal being vaccinated or may be an organism that produced an allergen or other antigen of the animal. Allergens are substances that cause allergic reaction, in this case in the animal which will be vaccinated against them. Many different materials may be allergens, such as animal dander and pollen, and the allergic reaction of individual animals will vary for any particular allergen. It is possible to induce tolerance to an allergen in an animal that normally shows an allergic response. The methods of inducing tolerance are well-known and generally comprise administering the allergen to the animal in increasing dosages. Further discussion of tolerance induction is given in the Barret textbook previously cited. Lastly, the host organism itself can serve as a source of genetic material when immunoregulatory genes or genes for other pharmacologically active substances are being expressed by the vectors.

Administration of a live vaccine of the type disclosed above to an animal may be by any known or standard technique. These include oral ingestion, gastric intubation, or broncho-nasal spraying. All of these methods allow the live vaccine to easily reach the GALT or BALT cells and induce antibody formation and are the preferred methods of administration. Other methods of administration, such as intravenous injection, that allow the carrier microbe to reach the animal's blood stream may be acceptable. Intravenous, intramuscular or intramammary injection are also acceptable with other embodiments of the invention, as is described later.

Since preferred methods of administration are oral ingestion, aerosol spray and gastric intubation, preferred carrier microbes are those that belong to species that home preferentially to any of the lymphoepithelial structures of the intestines or of the bronchii of the animal being vaccinated. These strains are preferred to be avirulent derivatives of enteropathogenic strains produced by genetic manipulation of enteropathogenic strains. Strains that home to Peyer's patches and thus directly stimulate production of IgA are most preferred. In animals these include specific strains of Salmonella, and Salmonella-$E.$ $coli$ hybrids that home to the Peyer's patches.

Recombinant DNA techniques are now sufficiently well known and widespread so as to be considered routine. In very general and broad terms, this method consists of transferring the genetic material, or more usually part of the genetic material, of one organism into a second organism so that the transferred genetic material becomes a permanent part of (recombines with) the genetic material of the organisms to which it is transferred. This usually consists of first obtaining a small piece of DNA from the parent organism either from a plasmid or a parent chromosome. A plasmid (also called an extrachromosomal element) is a hereditary unit that is physically separate from the chromosome of the cell. The DNA may be of any size and is often obtained by the action of a restriction endonuclease enzyme which acts to split DNA molecules at specific basepair sites. Following ligation to plasmid, phage or cosmid vectors to form recombinant molecules the recombinant molecules may be transferred into a host cell by various means such as transformation (uptake of naked DNA from the external environment, which can be artificially induced by the presence of various chemical agents, such as calcium ions). Other methods such as transduction are also suitable, wherein the recombinant DNA is packaged within a phage such as transducing phage or cosmid vectors. Once the recombinant DNA is in the carrier cell, it may continue to exist as a separate piece (generally true of complete transmitted plasmids) or it may insert into the host cell chromosome and be reproduced with the chromosome during cell division.

Although transferring genetic material is relatively straightforward, predicting which transfers will result in expressed genes is not yet possible. This selection process, however, does not present any difficulty to the present invention. Since the host microbe must express the transferred gene and thereby produce an antigen, a "shotgun" approach works well. Antibodies are first produced against the desired antigen, for example, fragments of cell membranes from pathogenic microbes, by standard techniques. DNA from the organism that is the source of the antigen is cleaved into multiple fragments by endonucleases, and the fragments are inserted randomly into carrier microbes that express antigens from the pathogen can be easily identified by their reaction with antibody against pathogen antigens. Antigen-expressing microbes can be selected and cloned to give the desired recombinant organism. Shotgun cloning is well known and is described in detail in Maniatis, T., et al., *Molecular Cloning* Cold Spring Harbor Laboratories (1982), which is herein incorporated by reference. The techniques of gene transfer are not considered to be part of this invention, and any method capable of producing recombinant organisms comprising genes from an organism that are expressed in avirulent microbes will suffice.

In cases where the species normally exchange genetic information more classical methods of gene transfer may be employed such as conjugation, transformation or transduction.

Derivatives of avirulent microbes are also contemplated to be within the scope of this invention. By derivative is meant sexually or asexually derived progeny and mutants of the avirulent strains including single or multiple base substitutions, deletions, insertions or inversions which retain the inability to produce functional adenylate cyclase and cAMP receptor protein with or without naturally occurring virulence plasmids. For example, strains such as Chi4062 and Chi4064 carry the gyrA mutation conferring nalidixic acid resistance which has been used herein as a convenient marker to follow strains following oral inoculation. However, drug resistance is not a desirable attribute for strains to be used as vaccines. Thus, the gyrA+ mutation can be easily removed by transducing the gyrA+ (conferring sensitivity to nalidixic acid) gene into strains by selecting for inheritance of a closely linked Tn10 and then removing Tn10 by selection for fusaric acid resistance.

The dosages required will vary with the antigenicity of the gene product and need only be an amount sufficient to induce an immune response typical of existing vaccines. Routine experimentation will easily establish the required amount. Multiple dosages used as needed to provide the desired level of protection.

The pharmaceutical carrier in which the vaccine is suspended or dissolved may be any solvent or solid or encapsulated in a material that is non-toxic to the inoculated animal and compatible with the carrier organism or antigenic gene product. Suitable pharmaceutical carriers include liquid carriers, such as normal saline and other non-toxic salts at or near physiological concentrations, and solid carriers, such as talc or sucrose and which can also be incorporated into feed for farm animals. Adjuvants may be added to enhance the antigenicity if desired. When used for administering via the bronchial tubes, the vaccine is preferably presented in the form of an aerosol.

Immunization with a pathogen derived gene product can also be used in conjunction with prior immunization with the avirulent derivative of a pathogenic microorganism acting as a carrier to express the gene product specified by a recombinant gene from a pathogen. Such parenteral immunization can serve as a booster to enhance expression of the secretory immune response once the secretory immune system to that pathogen-derived gene product has been primed by immunization with the carrier microbe expressing the pathogen derived gene product to stimulate the lymphoid cells of the GALT or BALT. The enhanced response is known as a secondary, booster, or anamnestic response and results in prolonged immune protection of the host. Booster immunizations may be repeated numerous times with beneficial results.

The above disclosure generally describes the present invention. A more complete understanding can be obtained by reference to the following specific examples which are provided herein for purposes of illustration only and are not intended to be limiting unless otherwise specified.

EXAMPLES

Example 1

This example demonstrates the construction of an avirulent microbe by the introduction of deletion mutations affecting cAMP synthesis and utilization.

Bacterial strains.

The *Salmonella typhimurium* strains used are listed in Table 1. They were maintained as frozen cultures suspended in 1% Bacto-peptone containing 5% glycerol and fast-frozen in dry ice-ethanol for storage in duplicate at −70° C. and also suspended in 1% Bacto-peptone containing 50% glycerol for storage at −20° C. for routine use.

Media.

Complex media for routine cultivation were L-broth (Lennox, *Virology* 1:190–206, (1965)) and Luria broth (Luria and Burrous, *J. Bacteriol.* 74:461–476 (1957)). Difco agar was added to Luria broth at 1.2% for base agar and 0.65% for soft agar. Penassay agar was used for routine enumeration of bacteria. Fermentation was evaluated by supplementing MacConkey base agar or Eosin methylene blue agar (Curtiss, *Genetics* 58:9–54 (1968)) with 1% final concentration of an appropriate carbohydrate.

TABLE 1
Bacterial strains

| Strain number | Parent strain/ plasmid | Relevant genotype | Derivation |
|---|---|---|---|
| χ3000 | LT2-Z/pStLT100 | prototroph | Charles Turnbough |
| χ3041 | SR-11/pStSR100 | virulent prototroph P22$^i$ | William Benjamin |
| χ3147 | LT2-Z/pStLT100 | gyrA1816 | spontaneous malidixic acid-resistant mutant of χ3000 |
| χ3181 | SR-11/pStSR100 | prototroph | mouse-passaged χ3041 |
| χ3306 | SR-11/pStSR100 | gyra1816 P22$^i$ | P22 HT int(χ3147) → χ3181 |
| χ3337 | SR-11 | gyrA1816 P22$^i$ | χ3306 cured of 100kb virulence plasmid |
| χ3456 | SR-11/PStSR101 | pStSR100::Tnminitet43 | P22 HT int(pStSR100::Tnminitet43 → χ3181 |
| PP1002 | LT2/pStLT100 | cya::Tn10 trpB223 | P. W. Postma; P22(PP991) → SB3507 (Postma et al., J. Bact 168: 1107–1111 |
| PP1037 | LT2/pStLT100 | crp773::Tn10 trpB223 | P. W. Postma; P22(PP1011) → SB3507 (Postma et al., |
| χ3395 | SR-11/pStSR100 | gyrA1816 cya::Tn10 | P22 HT int(PP1002) → χ3306 |
| χ3396 | SR-11/pStSR100 | gyrA1816 crp773::Tn10 | P22 HT int(PP1037) → χ3306 |
| χ4032 | SR-11/pStSR100 | gyra1816 Δcya-1 | FA$^r$ Tc$^s$ derivative of χ3395 |
| χ4055 | SR-11/pStSR100 | gyrA1816 Δcya-1 crp773::Tn10 | P22 HT int(PP1037) → χ4032 |
| χ4058 | SR-11 | gyrA1816 cya::Tn10 | P22 HT int(PP1002) → χ3337 |
| χ4060 | SR-11 | gyrA1816 Δcya-3 | FA$^r$ Tc$^s$ derivative of χ4058 |
| χ4061 | SR-11 | gyrA1816 Δcya-3 crp773::Tn10 | P22 HT int(PP1037) → χ4060 |
| χ4062 | SR-11 | gyrA1816 Δcya-3 Δcrp-2 | FA$^r$ Tc$^s$ derivative of χ4061 |
| χ4064 | SR-11/pStSR100 | gyrA1816 Δcya-1 Δcrp-1 | FA$^r$ Tc$^s$ derivative of χ4055 |

Synthetic media were minimal liquid (ML) and minimal agar (MA) supplemented with nutrients at optimal levels as previously described (Curtiss, *J. Bact.* 89:28–40, (1965)). Buffered saline with gelatine (BSG) (Curtiss, 1965 supra) was used routinely as a diluent.

Transduction.

Bacteriophage P22 HT int was routinely used for transduction using standard methods (Davis et al., "A Man. for Genet. Eng.-Adv. Bact. Genetics". Cold Spring Harbor Laboratory, Cold spring Harbor, N.Y., (1979)). An overnight culture of the donor strain was diluted 1:20 into prewarmed Luria-broth, grown for 60 minutes with shaking at 37° C. and then infected with P22 HT int at a multiplicity of 0.01. The infection mixture was shaken overnight for approximately 15 h, chloroform added and allowed to shake an additional 10 min at 37° C., and the suspension centrifuged (Sorvall RC5C, SS-34 rotor, 7,000 rpm, 10 min) to remove bacterial debris. The supernatant fluid containing the phage (ca. $10^{10}$/ml) was stored at 4° C. over chloroform. Tetracycline to a concentration of 12.5 micrograms/ml was used to select for transduction of Tn10-induced mutations.

Fusaric acid selection for deletion mutations.

The media and methods described by Maloy and Nunn (*J. Bact.* 145:1110–1112, (1981)) were used. Strains with Tn10-induced mutations were grown overnight in L-broth containing 12.5 micrograms tetracycline/ml at 37° C. to approximately $5 \times 10^8$ cfu/ml. Cultures were then diluted 1:40 into prewarmed L-broth without tetracycline and aerated at 37° C. to a titer of about $2 \times 10^9$ cfu/ml. Suitable numbers of cells (i.e., $10^7$–$10^8$) diluted into BSG were plated on fusaric acid containing medium and incubated 48 h at 37° C. Fusaric acid-resistant isolates were purified on the same selective medium. Single isolates were picked, grown and tested for tetracycline sensitivity on Penassay agar with and without 12.5 micrograms tetracycline/ml.

Mice.

Female BALB/c mice (Sasco, St. Louis, Mo.) were used for all infectivity and immunization experiments. Animals of 3 or 7 weeks of age were purchased and held for one week in a quarantined room prior to being used in experiments. Experimental mice were placed in Nalgene filter-covered cages with wire floors. Food and water were given ad libitum. The animal room was maintained at 22°–23° C. with a period of 12 hours illumination.

Animal infectivity.

The virulence of *S. typhimurium* strains was determined following peroral or intraperitoneal inoculation. Bacteria for inoculation in mice were grown overnight as standing cultures at 37° C. in L-broth. These cultures were diluted 1:50 into prewarmed L-broth and aerated at 37° C. for approximately 4 h to an $OD_{600}$ of about 0.8–1.0. The cells were concentrated 50-fold by centrifugation in a GSA rotor at 7,000 rpm for 10 min at 4° C. in a Sorvall RC5C centrifuge followed by suspension in BSG. Suitable dilutions were plated on Penassay agar for titer determination and on MacConkey agar with 1% maltose to verify the Cya/Crp phenotype.

For all peroral inoculations, mice were deprived of food and water for 4 h prior to infection. They were then given 30 microliters of 10% (w/v) sodium bicarbonate using a Pipetman P200 5 min prior to peroral feeding of 20 microliters of *S. typhimurium* suspended in BSG using a Pipetman P20. Food and water were returned 30 min after oral inoculation. Morbidity and mortality of mice were observed over a 30-day period.

Intraperitoneal inoculation of unfasted mice was performed using a 26-gauge needle to deliver 300 microliters of bacterial suspension diluted in BSG. Morbidity and mortality of mice were observed over a 30day period.

Evaluation of protection immunity.

In initial experiments, any mice that survived infection with any *S. typhimurium* mutant strain for 30 days were challenged on day 31 with $10^3$–$10^4$ times the $LD_{50}$ doses of the wild-type mouse-virulant *S. typhimurium* SR11 strain Chi3306 by the peroral route. Subsequently, groups of mice were perorally immunized with various doses of avirulent mutants and then challenged with various doses of virulent Chi3306 cells at various times after the initial immunization. Morbidity and mortality were observed throughout the experiment and for at least 30 days after challenge with Chi3306 cells.

Enumeration of viable *S. typhimurium* cells in vivo.

Colonization and persistence of wild-type and mutant *S. typhimurium* SR11 strains were determined following peroral inoculation of mice with approximately $1 \times 10^9$ cells by the methods described above. Titers of *S. typhimurium* cells were determined at 4, 24, 48, 72 and 96 hours and 7 days after peroral infection in the contents of the small intestine and colon and in homogenates of Peyer's patches (8–10), a 10 cm section of small intestinal wall located at the distal section of the ileum with Peyer's patches removed, and the colon wall. Titers of cells in homogenates of mesenteric lymph nodes and spleen were also determined. Mice were euthanized by $CO_2$ asphyxiation and the mesenteric lymph nodes, spleen, small intestine, and colon were immediately placed in chilled ML+ 15% sucrose minimal salts (MLS) which were held on ice. A petri dish containing 4.0 ml of chilled MLS was used to hold the small intestines while the Peyer's patches were removed with small surgical scissors. Peyer's patches were rinsed twice with 1 ml each of chilled BSG before placing into a glass screw-cap tube (15×100 mm) containing 1 ml chilled MLS and glass beads. The small intestine was then cut longitudinally and the contents and walls placed in a 50 ml disposable conical tube and chilled MLS was added to a 5.0 ml volume prior to vortexing for 1 min. A 10 cm section of small intestine was removed, rinsed twice in 5 ml BSG, and placed in a glass screw-cap tube (15×100 mm) containing 2.5 ml chilled MLS and glass beads. The contents of the small intestine were recovered from the chilled MLS used during longitudinal dissection and washing of the small intestine and added to the 50 ml disposable conical tube containing the small intestinal contents. A petri dish containing 4.0 ml of chilled MLS was used to hold the colon while it was cut longitudinally through the caecum. The contents of the colon and the colon wall were placed in a 50 ml final volume prior to vortexing for 1 min. The colon wall was then removed and rinsed twice in 5 ml BSG before placing into a glass screw-cap tube (15×100 mm) containing 2.5 ml chilled MLS and glass beads. The contents of the colon were collected from the chilled MLS used during longitudinal dissection and washing of the colon and added to the 50 ml disposable conical tube containing the colon contents. The mesenteric lymph nodes and connecting fatty tissue were placed in a glass screw-cap tube (15×100 mm) containing 1.0 ml chilled MLS and glass beads and vortexed. Spleens harvested at 96 h and 7 days are processed by placing directly into a Dounce pestle-type tissue homogenizer and grinding with 2.5 ml chilled MLS. Each tube with glass beads and tissue was vortexed for 4 to 5 min using a Super-mixer at high speed. Suspensions were diluted in BSG and plated on MacConkey agar containing 1% lactose and 40 micrograms nalidixic acid/ml. Total viable titers were determined by using the volumes of the suspensions, the dilutions, and the plate counts. MacConkey agars containing 1% of various carbohydrates were used to verify that the recovered organisms had the expected phenotype.

Constructions of *S. typhimurium* SR11 strains with cya and crp mutations.

The *S. typhimurium* SR11 strain Chi3041 was used to peroral infection of BALB/c mice. A noticeably ill animal was sacrificed after 5 days and the subsequently verified fully mouse-virulent isolate Chi3181 was recovered from a Peyer's patch. A gyrA mutation conferring resistance to nalidixic acid was introduced into Chi3181 by P22 transduction to yield Chi3306, the parent to all of the strains to be described herein (Table 1).

Since it has been shown that *S. typhimurium* isolates cured of the 100 kb virulence plasmid are fully able to attach to, invade and persist in Peyer's patches, but are defective in traversing to the mesenteric lymph nodes and spleen, cya and crp mutations were introduced into the plasmid-cured *S. typhimurium* SR11 strain Chi3337 as well as into the plasmid-containing SR11 derivative Chi3306. It should be emphasized that the reintroduction of the pStSR100 plasmid into Chi3337 completely restores its virulence (See Example 3), thus insuring that no secondary mutations arose in Chi3337 during the curing of the virulence plasmid.

Table 2 lists the phenotypic properties of all the mutant strains and their parents with regard to fermentation of sugars and growth on various carbon sources. The phenotypes are as expected based on published reports of the requirement for cyclic AMP and the cyclic AMP receptor protein for catabolic activities. (An exception is Chi4060 which behaved like a cya crp double mutant rather than a cya single mutant.) All cya/crp mutant strains lack fimbriae and flagella as expected based on previous results (Saier et al., *J. Bact.* 134(1):356–358, (1978); Yokota and Gots, *J. Bact.* 103:513– 16 (1970); and Komeda et al., *Mol. Gen'l. Genet.* 142:289– 298, (1975)). It is also evident that the presence of the pStSR100 plasmid had no effect on these phenotypes.

independent of the presence or absence of the pStSR100 plasmid grow much more slowly than the parental Chi3306 culture.

TABLE 3

Growth properties of bacterial strains.

| Strain number | Relevant genotype | Colony diameter (mm)[a] 40 h | 65 h | 87 h | Generation time[b] (min) |
|---|---|---|---|---|---|
| χ3306 | wild-type | 2.0 | 2.1 | 2.1 | 78 |
| χ3337 | wild-type | 2.0 | 2.1 | 2.1 | 82 |
| χ3395 | cya::Tn10 | 1.5 | 2.1 | 2.3 | 120 |
| χ3396 | crp773::Tn10 | 1.0 | 1.3 | 1.4 | 113 |
| χ4032 | Δcya-1 | 1.0 | 1.1 | 1.4 | 150 |
| χ4060 | Δcya-3 | 0.9 | 1.1 | 1.6 | 128 |
| χ4062 | Δcya-3 Δcrp-2 | 0.8 | 1.5 | 1.8 | 180 |
| χ4064 | Δcya-1 Δcrp-1 | 1.0 | 1.7 | 2.0 | 150 |

[a]Colonies distributed ~100 per plate on MA + 0.5% glucose
[b]Growth in ML + 0.5% glucose Virulence of mutant strains for mice.

Preliminary information on virulence of mutant strains was obtained by infecting individual mice with either $10^5$ mutant cells intraperitoneally or $10^8$ mutant cells perorally and recording morbidity and mortality. Since Chi3395 with the cya::Tn10 mutation and Chi3396 with the crp::Tn10 mutation were apparently avirulent and since mice surviving infection with either become immune to challenge with wile-type Chi3306 cells, further studies on the virulence of Chi3395 and Chi3396 were undertaken. Table 4 contains data which shows that mice survive infection with about $10^3$ times the $LD_{50}$ dose of either the cya::Tn10 mutant or the crp::Tn10 mutant. Studies were then initiated with strains in which the Tn10 and adjacent DNA sequences had been deleted. Table 5 presents data on morbidity and mortality of mice infected perorally with *S. typhimurium* wild-type, delta-cya and delta-crp strains. It is evident that irrespective of age of mice at the time of infection all mice survive TABLE 2
Fermentation and growth properties of bacterial strains

| Strain number | Cya Crp pheno- type | Fermentation phenotype on MacConkey agar containing:[a] | | | | | | | | Growth on Minimal agar containing: | | | | | | | | |
|---|---|---|---|---|---|---|---|---|---|---|---|---|---|---|---|---|---|---|
| | | Frc | Gal | Glu | Glyc | Mal | Mtl | Mel | Srl | Cit | Gal | Glu | Glyc | Mal | Mtl | Mel | Srl | Suc |
| χ3306 | + + | + | + | + | + | + | + | + | + | + | + | + | + | + | + | + | + | + |
| χ3395 | − + | + | + | + | + | − | + | + | + | − | + | + | + | − | + | + | + | − |
| χ3396 | + − | + | +/− | + | − | − | − | − | − | + | + | − | − | − | − | − | − |
| χ4032 | − + | + | + | + | + | − | + | + | + | − | + | + | + | − | + | + | + | − |
| χ4060 | − + | + | − | + | − | − | − | − | − | + | + | − | − | − | − | − | − |
| χ4062 | − − | + | − | + | − | − | − | − | − | + | + | − | − | − | − | − | − |
| χ4064 | − − | + | − | + | − | − | − | − | − | + | + | − | − | − | − | − | − |

[a]: += positive for fermentation or growth; +/− = intermediate pink or haze-type growth; − = negative for fermentation or growth At each step in the construction following selection of a fusaric acid-resistant tetracycline-sensitive derivative, an investigation as to whether tetracycline-resistant revertants/mutants could be recovered at frequencies higher than could be observed for the parental Chi3306 strain was conducted. In all cases, such tetracycline-resistant revertants/mutants were not observed.

Colony diameters on MA containing 0.5% glucose as a function of incubation time and generation times in ML containing 0.5% glucose of several of the mutant strains and their parent are presented in Table 3. It is evident that the delta-cya strains with or without the delta-crp mutation and infection with 1000–4000 wild-type $LD_{50}$ doses of any of the mutant strains. The information in Table 5 pertaining to avirulence of the pStSR100-cured derivative Chi3337 are in accord with the more thorough studies presented in Example 3.

Table 6 presents additional data pertaining to infection with delta-cya and delta-crp delta-crp strains Chi4060 and Chi4062 (plasmid-cured) and Chi4032 and Chi4064 (plasmid-containing) which demonstrate that mice infected perorally with $1\times10^9$ bacteria grow essentially as well as do mice that remain uninfected.

Table 7 presents data for intraperitoneal challenge of the *S. typhimurium* mutants. Mice survived infection with $10^2$ to $10^3$ times the wild-type $LD_{50}$ dose for the various mutant strains. At higher doses, illness was observed which may be due in part to effects of endotoxin.

TABLE 4

Virulence of *S. typhimurium* SR-11 cya::Tn10 and crp773::Tn10 in BALB/c female mice 30 days after peroral inoculation

| Strain number | Relevant genotype | Inoculating dose (cfu) | Age of mice[a] | Survival live/total | Mean day of death[b] | Health[c] |
|---|---|---|---|---|---|---|
| χ3306 | wild-type | $2.5 \times 10^5$ | 8 wk | 2/5 | 7 | scruffy |
| χ3395 | cya::Tn10 | $1.3 \times 10^9$ | 8 wk | 2/5 | 17 | scruffy |
| χ3396 | crp773::Tn10 | $2.4 \times 10^8$ | 8 wk | 5/5 | — | healthy |

[a] at time of immunization.
[b] of animals that died.
[c] healthy — no noticeable signs of disease; scruffy — noticeably ill.

TABLE 5

Morbidity and mortality 30 days after peroral challenge of BALB/c mice with *S. typhimurium* SR-11 Δcya and/or Δcrp strains

| Strain number | Relevant genotype | pStSR100 | Inoculating dose (cfu) | Age of mice[a] | Survival live/total | Health[b] |
|---|---|---|---|---|---|---|
| χ3306 | wild-type | + | $2.5 \times 10^5$ | 8 wk | 3/6[c] | scruffy |
| χ3337 | wild-type | − | $5.0 \times 10^8$ | 8 wk | 6/6 | scruffy |
| χ4032 | Δcya-1 | + | $1.3 \times 10^9$ | 4 wk | 6/6 | healthy |
| χ4032 | Δcya-1 | + | $1.3 \times 10^9$ | 8 wk | 6/6 | healthy |
| χ4060 | Δcya-3 | − | $7.8 \times 10^8$ | 4 wk | 6/6 | healthy |
| χ4060 | Δcya-3 | − | $7.8 \times 10^8$ | 8 wk | 6/6 | healthy |
| χ4062 | Δcya-3 Δcrp-2 | − | $1.2 \times 10^9$ | 4 wk | 6/6 | healthy |
| χ4062 | Δcya-3 Δcrp-2 | − | $1.2 \times 10^9$ | 8 wk | 6/6 | healthy |
| χ4064 | Δcya-1 Δcrp-1 | + | $1.2 \times 10^9$ | 4 wk | 6/6 | healthy |
| χ4064 | Δcya-1 Δcrp-1 | + | $1.2 \times 10^9$ | 8 wk | 6/6 | healthy |

[a] at time of challenge.
[b] healthy — no noticeable signs of disease; scruffy — noticeably ill.
[c] Mean day of death = 7

TABLE 6

Evaluation of growth of 8 week-old BALB/c female mice 30 days after administering Δcya Δcrp *S. typhimurium* SR-11

| Strain number | Relevant genotype | pStSR100 | Inoculating dose (cfu) | Weight (in grams) at: Time of infection | Weight (in grams) at: 30 days post-infection |
|---|---|---|---|---|---|
| Control | | | uninfected | 19.2 ± 0.3 | 21.8 ± 0.3 |
| χ3395 | cya::Tn10 | + | $1.3 \times 10^9$ | 17.8 ± 0.5 | 18.9 ± 3.0 |
| χ3396 | crp773::Tn10 | + | $2.4 \times 10^8$ | 18.9 ± 1.1 | 20.5 ± 1.3 |
| χ4032 | Δcya-1 | + | $8.6 \times 10^8$ | 19.8 ± 0.5 | 21.4 ± 0.5 |
| χ4060 | Δcya-3 | − | $8.8 \times 10^8$ | 19.4 ± 0.6 | 21.4 ± 1.4 |
| χ4062 | Δcya-3 Δcrp-2 | − | $6.8 \times 10^8$ | 20.1 ± 0.2 | 21.7 ± 0.4 |
| χ4064 | Δcya-1 Δcrp-1 | + | $1.0 \times 10^9$ | 19.9 ± 0.4 | 21.9 ± 0.8 |

TABLE 7

Morbidity and mortality 30 days after introperitoneal challenge of 8 week-old BALB/c female mice with S. typhimurium SR-11 Δcya and/or Δcrp strains

| Strain number | Relevant genotype | pStSR100 | Challenge dose (cfu) | Survival live/total | Mean day of death[a] | Health[b] |
|---|---|---|---|---|---|---|
| χ3306 | wild-type | + | <50 | 3/6 | 7 | scruffy |
| χ3395 | cya::Tn10 | + | $1.0 \times 10^4$ | 0/5 | 12 | none |
|  |  |  | $1.0 \times 10^5$ | 1/5 | 7 | scruffy |
|  |  |  | $1.0 \times 10^6$ | 0/5 | 3 | none |
| χ3396 | crp773::Tn10 | + | $1.9 \times 10^4$ | 5/5 | — | healthy |
|  |  |  | $1.9 \times 10^5$ | 4/5 | 18 | moderate |
|  |  |  | $1.9 \times 10^6$ | 1/5 | 12 | scruffy |
| χ4062 | Δcya-3 Δcrp-2 | − | $1.0 \times 10^4$ | 5/5 | — | healthy |
|  |  |  | $1.0 \times 10^5$ | 5/5 | — | healthy |
|  |  |  | $1.0 \times 10^6$ | 0/5 | 10 | none |
| χ4064 | Δcya-1 Δcrp-1 | + | $1.6 \times 10^4$ | 5/5 | — | healthy |
|  |  |  | $1.6 \times 10^5$ | 2/5 | 14 | scruffy |
|  |  |  | $1.6 \times 10^6$ | 0/5 | 16 | none |

[a]of animals that died.
[b]healthy — no noticeable signs of disease; moderate — moderately ill; scruffy — noticeably ill.

Effectiveness of immunization with avirulent mutants.

Table 8 presents data on the ability of the different S. typhimurium delta-cya and delta-cya delta-crp mutants to induce immunity to subsequent peroral challenge with $10^4$ times the $LD_{50}$ doses of fully virulent S. typhimurium SR11 Chi3306 cells. Under these worse case challenges, many of S. typhimurium to attach to, invade and persist in the Peyer's patches at least for a period of time sufficient to induce protective immunity (FIG. 1) but no impair ability to reach or survive in the spleen (FIG. 2).

TABLE 8

Effectiveness of immunization with avirulent S. typhimurium SR-11 Δcya Δcrp mutants in protecting against challenge with $2 \times 10^9$ cfu wild-type virulent S. typhimurium SR-11[a]

| Strain number | Relevant genotype | pStSR100 | Dose (cfu) of immunizing strain | Age of mice[b] | Survival live/total | Mean day of death[c] | Health[d] |
|---|---|---|---|---|---|---|---|
| χ4032 | Δcya-1 | + | $1.3 \times 10^9$ | 4 wk | 6/6 | — | moderate |
| χ4032 | Δcya-1 | + | $1.3 \times 10^9$ | 8 wk | 5/6 | 46 | moderate |
| χ4060 | Δcya-3 | − | $7.8 \times 10^8$ | 4 wk | 6/6 | — | moderate |
| χ4060 | Δcya-3 | − | $7.8 \times 10^8$ | 8 wk | 6/6 | — | moderate |
| χ4062 | Δcya-3 Δcrp-2 | − | $1.2 \times 10^9$ | 4 wk | 5/6 | 46 | moderate |
| χ4062 | Δcya-3 Δcrp-2 | − | $1.2 \times 10^9$ | 8 wk | 5/6 | 48 | moderate |
| χ4064 | Δcya-1 Δcrp-1 | + | $1.2 \times 10^9$ | 4 wk | 6/6 | — | healthy |
| χ4064 | Δcya-1 Δcrp-1 | + | $1.2 \times 10^9$ | 8 wk | 6/6 | — | healthy |

[a]Thirty days after immunization of 4 or 8 week-old mice with the strains indicated, mice were challenged with a per oral dose of $2.0 \times 10^9$ cfu of χ3306 wild-type virulent S. typhimurium SR-11.
[b]at time of immunization.
[c]following immunization of animal that died.
[d]healthy — no noticeable signs of disease or illness; moderate — moderately ill.

the mice displayed moderate illness with decreased food consumption except mice immunized with Chi4064 which remained healthy and ate and grew normally. Sacrifice of all animals (even those immunized with Chi4064) 30 days post-challenge revealed spleenomeglia and ability to recover the Chi3306 wild-type challenge strain but not the avirulent delta-cya or delta-cya delta-crp vaccine strains. In contrast, spleenomeglia and recovery of the challenge strain was not observed when mice immunized with approximately $1 \times 10^9$ Chi4064 were challenged with only 100 to 1000 $LD_{50}$ doses of the fully virulent Chi3306 parent strain.

Tissue trophism and persistence of avirulent mutants in vivo.

FIGS. 1 and 2 present data on recovery of the delta-cya delta-crp strain Chi4064 in comparison to recovery of the nalidixic acid-sensitive wild-type strain Chi3456 (Tn minitet-labeled; see Table 1) as a function of time following peroral inoculation. It is evident that the delta-cya and delta-crp mutations do not significantly impair the ability of Genetic stability of avirulent mutants.

Strains to be orally administered as live vaccines must have complete stability with regard to both their avirulence and their immunogenic attributes. Several of the candidate vaccine strains have therefore been grown in L-broth to late log phase with aeration, concentrated 50-fold and plated at various dilutions on a series of minimal agar media containing carbon sources that do not support the growth of the parent mutant (Table 2). A duplicate set of plates was exposed to ultraviolet light at an intensity that caused 70% cell death. Spontaneous revertants/mutants were observed at low but measurable frequencies (Table 9) in the delta-cya strain Chi4032 and at higher frequencies in the delta-cya strain Chi4060; many of these revertants were able to grow on most carbon sources and were therefore likely to be crp* (Schalte and Postma, J. Bact. 141:751–57 (1980); Garges and Adhya, Cell 41:745–51 (1985)) or csm (Melton et al., Mol. Gen'l. Genet. 182:480–89 (1981)) mutations that permit CRP to activate transcription in the absence of cyclic AMP. Revertants/mutants from the delta-cya delta-crp strains such as Chi4064 were extremely rare (Table 9) and although able to grow on the carbon source (i.e., mannitol) on which they were selected, failed to grow on any of the other carbon sources the original strain failed to utilize (Table 2). These revertants/mutants undoubtedly have promoter mutations, causing transcription of the specific gene/operon to be independent of CRP. Ultraviolet light exposure did not enhance mutation/reversion frequencies.

Six revertants/mutants have been evaluated for virulence. Four mice were used to test each revertant. One received a peroral dose of $10^5$ cells, another a peroral dose of about $10^8$ cells, another an intraperitoneal dose of $10^2$ cells, and another an intraperitoneal dose of $10^5$ cells. In all instances, the four revertants from delta-cya mutants and the two other hand, immunization with Chi4064 might be less well tolerated than immunization with Chi4062 in young animals or in individuals that are malnourished or otherwise compromised. In this regard, if two immunizations were desirable, one could immunize first with Chi4062 and then with Chi4064.

A desired use of vaccine strains such as Chi4062 and Chi4064 is to serve as carriers to target colonization or virulence antigens expressed by genes from other pathogens to the gut-associated lymphoid tissue so as to induce a generalized secretory immune response and humoral and cellular immunity, if that should be desired. Therefore a variety of cloning vectors have been introduced into Chi4062 and Chi4064 and these plasmids exhibit a stability equal to or greater than in the wild-type parent strains. In

TABLE 9

Spontaneous reversion/mutation of Δcya Δcrp strains as revealed by plating 50-fold concentrated cultures on minimal agar with 0.5% final concentration of various carbohydrates

| Strain number | pStSR100 | Relevant genotype | Reversion frequency: | | | | | |
|---|---|---|---|---|---|---|---|---|
| | | | Mtl | Srl | Mal | Cit | Suc | Mel |
| χ4032 | + | Δcya-1 | $3.0 \times 10^{-5}$ | $3.0 \times 10^{-5}$ | 0 | 0 | 0 | 0 |
| χ4060 | − | Δcya-3 | TMTC[a] | TMTC | $2.0 \times 10^{-7}$ | $2.0 \times 10^{-7}$ | $2.0 \times 10^{-7}$ | TMTC |
| χ4062 | − | Δcya-3 Δcrp-2 | $2.7 \times 10^{-8}$ | 0 | 0 | 0 | 0 | 0 |
| χ4064 | + | Δcya-1 Δcrp-1 | $6.0 \times 10^{-8}$ | 0 | 0 | 0 | 0 | 0 |

[a]TMTC = Too many to count revertants of delta-cya delta-crp strains retained the avirulence of their parent since all 32 mice remained healthy with no noticeable illness. It therefore appears that the avirulence of delta-cya strains cannot be solely due to defective carbohydrate catabolism.

The above result evidences the construction of a number of derivatives of the mouse virulent *S. typhimurium* SR11 strain Chi3306 that lack the ability to synthesize adenylate cyclase and the cyclic AMP receptor protein and which do or do not possess the pStSR100 virulence plasmid. Although all strains are avirulent by the peroral route of inoculation and all induce a high level of protective immunity against subsequent challenge with virulent *S. typhimurium* wild-type cells, Chi4062 and Chi4064 which contain both delta-cya and delta-crp mutations are preferred. The use of the double mutant with the deletion of the crp gene precludes recovery of crp* mutations that permit transcription of genes and operons requiring activation by the CRP protein in the absence of any need to cyclic AMP. Similarly the absence of the crp gene also precludes the recovery of cms suppressor mutations that are closely linked to the crp gene, and which can also obviate the need for cyclic AMP. Even though the delta-cya crp* or cms revertant strains tested remained avirulent, enough independent revertant isolates have not been tested for virulence to conclude that virulence could not be restored; therefore, the delta-crp mutation should preclude such restoration of virulence no matter how unlikely such changes might be. In addition, the delta-crp::Tn10 mutation significantly reduces the virulence of *S. typhimurium* (Table 4) and therefore in the unlikely event that the delta-cya mutation was lost by some type of gene transfer event, the delta-crp mutation would still render the strain avirulent.

The vaccine strain Chi4064, which still possesses the pStSR100 plasmid, induces a higher level of immunity than does the plasmid-free strain Chi4062 (Table 8). This is undoubtedly due to the increased ability of Chi4064 (FIGS. 1 and 2) and plasmid-containing strains in general to achieve higher titers and persist longer than plasmid-free strains in mesenteric lymph nodes and spleen (see Example 3). On the fact, the slower rate of growth of Chi4062 and Chi4064 (Table 3) undoubtedly enhances the ability of plasmid replicons to keep up with chromosomal replication to insure that progeny cells contain plasmids. In addition, a variety of recombinant derivatives have been constructed and it was found that the colonization of *S. mutans* and *S. sobrinus* to the salivary glycoprotein-coated tooth surface (Curtiss, *J. Dent. Res.* 65:1034–1045 (1986)) is expressed to a higher level in the delta-cya crp mutants than in *S. typhimurium* strains with other mutations conferring avirulence.

Example 2

This example illustrates how the delta-cya, delta-crp mutations may be introduced into other Salmonella species to render said species avirulent and thus useful as vaccine components.

Salmonella species useful for practicing this embodiment of the invention include *S. arizona* and *S. gallinarum* as avian Salmonella strains. *S. choleraesuis* as a porcine-specific Salmonella, *S. dublin* as a bovine-specific Salmonella, and a number of *S. typhimurium* derivatives that have been isolated from chickens, turkeys, veal calves, pigs and horses. These strains can be used to construct delta-cya delta-crp mutants with and without virulence plasmids to evaluate protective immunity first in mice, and then in particular animal host species. These avirulent Salmonella derivatives can also be used to construct bivalent live vaccine strains for stimulation of protective immunity against the colonization and virulence proteins of other bacterial pathogens. Specifically, vaccines against *B. avium* and *E. coli*, two respiratory pathogens which are responsible for high morbidity and mortality in poultry and *Streptococcus equi*, which causes strangles in horses may be prepared.

Construction of Avirulent Salmonella Strains

*S. typhimurium* LT-2 strains that possess cya::Tn10 or crp::Tn10 with the delta[gal-uvrB]1005 mutation that renders a smooth or rough phenotype dependent upon the presence or absence of galactose, respectively, in the culture medium are used to generate the delta-cya delta-crp genotype. Transduction with P22 HT int is used to introduce the cya::Tn10 and crp::Tn10 mutations into strains of *S. typhimurium* obtained from various hosts and into *S. typhi, S. paratyphi* and other Salmonella with similar 0 antigens. The rough-specific generalized transducing phage P1L4, is employed to introduce the Tn10-induced mutations into *S. arizona, S. gallinarum, S. dublin,* and *S. choleraesuis*. P1L4 transduction of the Salmonella species described above requires isolation of rough mutants. Selection for 2-deoxygalactose resistance results in galE mutants. The galE defect can ultimately be eliminated by transduction with P1L4 propagated on a rough mutant with the wild-type $gal^+$ gene.

Stable deletion mutants are isolated by selection for fusaric acid-resistant derivatives of strains containing the Cya::Tn10 and/or crp::Tn10 insertion mutations. Fusaric acid-resistant derivatives are tetracycline sensitive due to imprecise excision of the transposon and adjacent host chromosomal genes. When successive use of Tn10 is desired, it is necessary to verify that the fusaric acid-resistant isolates have completely lost Tn10, for example, by using a lambda::Tn10 vector as a hybridization probe.

Salmonella strains cured of the virulence plasmid are constructed by using procedures and genetic tools developed for *S. typhimurium.* (See Examples 1 and 3). Tnmini-tet described by Way et al., (*Gene* 32:369–79 (1984)) is employed at this stage of construction. This transposon which lacks transposase and cannot spontaneously delete is inserted in the virulence-associated region of the 100 kb virulence plasmid that is probably homologous to the virulence plasmids of *S. dublin, S. gallinarum* and *S. choleraesuis* (Popoff et al., *Ann. Microbiol.* (Inst. Pasteur) 135A:389–398 (1984)). The transposon insertions are transduced into the homologous sequences of galE mutants of these other species. Tnmini-tet labeled virulence plasmids are cured by growing bacteria in novobiocin, a DNA gyrase inhibitor, at elevated temperatures of approximately 43° C. Curing of virulence plasmids can be verified by hybridization of cured derivatives with $^{32}P$-labeled native virulence plasmid.

All strains constructed are evaluated for stability of the genetic attributes and to determine that the phenotype displayed in *S. typhimurium* mutants is displayed in other Salmonella species. A last step to facilitate studies in animals is to introduce a drug resistance marker to assist in following the Salmonella strain during animal experimentation. Ordinarily resistance to either nalidixic acid or rifampicin is used since these resistances are not prevalent in the normal flora of mice, chickens, or turkeys.

Introducing some of the transposon-induced mutations into some of the Salmonella species by transduction may be impossible. Alternatively, conjugation may be beneficially employed wherein the transposon-induced mutation is cloned on a plasmid that can be mobilized from an Hfr with an integrated IncF or IncP plasmid into the Salmonella. Transformation provides yet a further alternative wherein the steps of selection for recombination of the sequence into the chromosome, elimination of the plasmid and verification of the precise genetic lesion are undertaken.

Evaluation of Immunogenicity, Colonization and Persistence

The avirulent Salmonella strains constructed above may be evaluated in mice using peroral inoculation, gastric intubation, or intraperitoneal injection.

The procedure is initiated by growing Salmonella strains to log phase and concentrating them to nearly $10^{10}$ cells/ml in a buffered saline with gelatin. Animals to be inoculated perorally or by gastric intubation are deprived of food and water for 4 hours prior to inoculation. Sodium bicarbonate is administered to mice 5 minutes before the inoculation to neutralize stomach acidity. Food and water are given back to the mice 30 minutes after inoculation. Based on previous experiments with these mutant strains of *S. typhimurium* in mice, ordinarily challenges with mice are with $10^3$ $LD_{50}$ doses. This might not be practical if the wild-type of the various Salmonella species do not given $LD_{50}$s as high as already observed for the mouse-virulent *S. typhimurium.* This becomes more of a problem for the peroral route of inoculation since administering more than $10^9$ organisms is difficult. Intraperitoneal inoculations may also be done at doses up to the level that would result in endotoxic shock (approximately $10^7$ cells). The weight and health condition of animals are monitored for one month.

Mice inoculated with the mutant Salmonella strain which survive for 30 days, are challenged with $10^3$ $LD_{50}$s of the virulent Salmonella parent strain by the peroral or intraperitoneal route. The health condition of the infected animals is followed daily with periodic evaluation for rate of growth. Prior to challenge, saliva samples are taken by pilocarpine stimulation, and each animal bled to collect serum. Quantitative titers of secretory IgA and IgG in saliva and of IgA and IgG in serum against Salmonella surface antigens are determined. The effect of secondary immunization on antibody titers and on persistence of immunity is also noted.

Vaccine strains which are avirulent, induce a high level of immunity and do not adversely affect weight gain, are used to determine the quantitative titers of the strain attached to the walls of the small bowel and colon and present in Peyer's patches, the small intestine and colon contents, and mesenteric lymph nodes, and in the spleen at 4, 24, 48, 72, and 96 hours and at weekly intervals thereafter if that should be necessary. This information is correlated with data on the immune response obtained.

Strains which are avirulent and immunogenic in mice, are then tested in the suitable animal species, e.g., *S. arizona, S. gallinarum* and avian *S. typhimurium* strains in chicks and turkey poults. Following evaluation of avirulence and immunogenicity in avian hosts, titers of virulent Salmonella in the crop, ceacum and Bursa of Fabricious are determined in addition to the tissues examined in mice.

Construction and Testing of Bivalent Vaccine Strains to Immunize Against *Bordetella avium*

Vaccines against *B. avium* should express the surface structures involved in colonization and the antigenic but not toxic determinants of dermonecrotic toxin vaccines to surface proteins should produce immunity by blocking colonization of the trachea while antibodies to dermonecrotic toxin should neutralize its adverse effects. Although the *B. avium* surface structures involved in colonization are not known, the availability of gene libraries of *B. avium* in lambda gt11 expression vectors and transposon-induced *B. avium* mutants enable isolation and identification of genes encoding the surface proteins. By introducing the recombinant plasmids containing genes for surface proteins and/or dermonecrotic toxin determinants into an avirulent Salmonella, one can select a bivalent strain which induces protective immunity by preventing colonization (and thus identify genes involved in colonization) or by neutralizing toxin.

The genes for *B. avium* outer membrane proteins and/or dermonecrotic toxin are transferred to appropriate avirulent *S. arizona, S. gallinarum,* and/or *S. typhimurium* derivatives via transformation according to the method of Curtiss (Manual of Meth. in Bacteriol., ASM. Washington, D.C. (1981)), and expression of these proteins are examined using Western blot methods (Towbin et al., *Proc. Natl. Acd. Sci. (USA)* 76:4350–54 (1979)). A 5 minute heat shock at 50° C. prior to transformation will be used to overcome any restriction barrier in Salmonella. Previous reports have indicated that Bordetella genes do not express efficiently in *E. coli* unless they are transcribed from an *E. coli* promoter. Such problems with expression of *B. avium* genes and translocation of the proteins to the outer membrane of Salmonella are eliminated by using a recombinant vector in which the gene will be fused to the *E. coli* lamb or ompA gene. In addition, the *B. avium* proteins would translocate to the outer membrane of Salmonella and enhance the probability of stimulating a strong immune response once the bivalent vaccine strain colonizes the Peyer's patches. Once *B. avium* genes are inserted into Salmonella, the recombinant clones are analyzed for expression of the genes by colony immunoblots using specific antibody and electron microscopy of immunolabeled Salmonella as disclosed by Chorbit et al., *EMBO J.* 5:3029–37 (1986).

One to three-day old poults are immunized perorally with the bivalent vaccine and serum and respiratory secretions are monitored to determine the type [IgY (IgG, 7S Ig), IgM, and IgA (IgB)] and quantity of the antibody response. Immunized and nonimmunized poults are compared for weight loss to monitor possible side-effects of the bivalent vaccine. In addition, turkey poults are challenged by intranasal inoculation with $10^9$ virulent *B. avium* or by exposure to infected birds. Challenged turkey poults are observed for disease, necropsied, and examined for tracheal tissue damage and changes in titers of the organism.

If a mucosal immune response against *B. avium* is inadequate to protect very young chickens and turkeys, breeding hens can be immunized with avirulent Salmonella expressing *B. avium* colonization and/or virulence antigens to permit egg transfer to maternal antibodies. Such treatment would augment immunity to *B. avium* with the young chicks or turkey poults are maturing. A protective peroral immunization employing the same recombinant carrier may also be administered during maturation.

Construction and Testing of Bivalent Vaccine
Strains to Immunize Against avian *E. coli*

Recombinant clones that endow avirulent *E. coli* with increased virulence or the ability to colonize air sacs of chicks are introduced into avirulent strains of *S. gallinarum* and/or *S. typhimurium* by methods described above. The expression of virulence determinants on the Salmonella cell surface is determined by fluorescent antibody techniques, but it should be noted that *E. coli* cell surface determinants are likely to be expressed on the surface of Salmonella.

Chickens are immunized perorally with the bivalent vaccine strain and challenged by injecting virulent *E. coli* into the caudal air sac. If septicemia does not develop, birds are necropsied to determine if ability to colonize the air sac has been affected. Subsequently, a comprehensive study of the types, quantity, and duration of the antibody response in the respiratory secretions and serum as described above for turkey poults in conducted.

Techniques for vaccine administration and evaluation are the same as described previously for the *B. avium* vaccine.

Construction and Testing of Bivalent Vaccine
Strains to Confer Immunity Against *Streptococcus equi*

Avirulent derivatives of *S. typhimurium* expressing the *S. equi* M protein have been constructed.

DNase I generated random fragments of the *S. egui* M protein gene are cloned into a lambda gt11 expression vector. The library is sequentially screened with antiserum against the M protein fragments that elicit protective immunity and antiserum against the M protein determinants present in the immune complexes of horses with purpura hemorrhagica. Cloned genes that express the protective, but not the purpuragenic, determinants are selected for fusion to either the lamb or ompA gene. The immune response against avirulent Salmonella carrying those determinants is first investigated in mice and then in ponies or horses.

The availability of the described Salmonella strain expressing on its surface the relevant epitopes of the M protein of *S. equi* constitutes a very effective way of stimulating a mucosal nasopharyngeal protective immune response against strangles in the horse. The dissection of the purpuragenic determinants of the M protein contribute to the safety of the vaccine.

Example 3

This Example illustrates the effect of virulence-plasmid deletion on the immunogenicity and virulence of several Salmonella strains.

Bacterial Strains

The bacterial strains used in this Example are listed in Table 10 along with plasmic descriptions. Three lines of *S. typhimurium* strains were used: mouse-passaged, virulent strains SR-11 and SL1344 and the lesser virulent strain LT2. *Escherichia coli* HB101 and C600 were used in genetic manipulations.

Culture media and growth conditions.

Unless otherwise stated, bacteria were grown in L broth or on L agar plates (Lennox, *Virology* 1:190–206 (1955)) supplemented with appropriate antibiotics at the following concentrations (micrograms/ml): ampicillin (Amp)—100–200, tetracycline (Tet)—12.5–25, chloramphenicol (Chl)—30, kanamycin (Kan)—50, streptomycin (Str)—50, and nalidixic acid (Nal)—50. For adherence, invasion, and macrophage infection some cultures were grown in Brain Heart Infusion broth (Difco, Detroit) because this medium increased bacterial adherence to the mammalian cells used. All cultures were grown overnight at 37° C. in static broths of the appropriate medium and were subcultured into shaking broths until late logarithmic phase of growth ($OD_{600}$ approximately 0.4–0.7).

Genetic exchange.

Transformation was performed by using the method of Bagdasarian and Timmis (*Curr. Top. Microbiol. Immunol.* 96:47–67 (1981)). Phage P22 HT int-mediated transduction was performed as described by

TABLE 10
Bacterial Strains

| Strain | | 100 kb plasmid | Genotype | Description |
|---|---|---|---|---|
| *S. typhimurium:* | | | | |
| LT2-Z | χ3000 | pStLT100 | wild-type | from C. Turnbough (69) |
| | χ3147 | pStLT100 | gyrA1816 | spontaneous Nal$^r$ derivative of χ3000 |
| | χ3344 | — | | 100 kb plasmid-cured χ3000 |
| | χ3347 | pStLT101 | | pStLT101 (Tnmini-tet-labeled pStLT100 obtained by transposition from pNK561) transformed into χ3344, Tet$^r$ |
| | χ3477 | — | hsdL6, Δ[gal-uvrB]-1005, flaA66, rpsL120 xyl-404, lamB$^+$(*E. coli*), Δ[zja::Tn10], hsdSA29 | used to obtain Rc chemotype LPS; S.A. Tinge and R. Curtiss (unpublished); Δ[galE-uvrB]-1005 obtained from B.A.D. Stocker in P22 HTint lysate from SL54000 |
| | χ3181 | pStSR100 | | SR-11 (57) isolated from Peyer's patch of an infected mouse; from Suzanne Michalek |
| | χ3306 | pStSR100 | gyrA1816 | gyrA1816 transduced into χ3181 from χ3147; mouse-passaged |
| | χ3337 | | gyrA1816 | 100 kb plasmid-cured χ3306 |
| | χ3338 | pStSR101 | gyrA1816 | pStSR101 (Tnmini-tet-labeled pStSR100 obtained by transduction from χ3000[pStLT101]) transformed into χ3337, Tet$^r$ |
| | χ3456 | pStSR101 | | χ3181 with Tnmini-tet-labeled pStSR100 obtained by transduction from χ3000(pStLT101), Tet$^r$ |
| SL1344 | χ3042 | pStSL100 | rpsL, hisG | from B.A.D. Stocker |
| | χ3339 | pStSL100 | rpsL, hisG | mouse-passaged χ3042 |
| | χ3340 | — | rpsL, hisG | 100 kb plasmid-cured χ3339 |
| | χ3351 | pStSR101 | rpsL, hisG | pStSR101 (Tnmini-tet-labeled pStSR100) transformed into χ3340, Tet$^r$ |
| *E. coli:* | | | | |
| K12 | | | F$^-$, thr-1, leuB6, tonA1, lacY1, λ$^-$, gyrA, thi-1 | spontaneous Nal$^r$ derivative of C600 |
| HB101 | | | F$^-$, ara-14, leuB6, proA2, lacY1, gluV44, galK2, λ$^-$, recA13, rpsL20, xyl-5, mtl-1, thi-1, hsdS20 (r$_B$-, m$_B$-) | |

Schmeiger (*Mol. Gen'l Genet.* 119:75–88 (1972)). Conjugations were performed either by plate matings or filter matings (Willetts, *Meth. in Microbiol.* 17:33–58, (1984)).

DNA manipulations. Large scale and rapid minilysate plasmid extractions were performed using the method of Birnboim (*Meth. Enzymol.* 100:243–255 (1983)). Cesium chloride density gradient centrifugation, Southern blot hybridization, colony blot hybridization, and gel electrophoresis were performed using standard procedures. Nick-translation of DNA with [gamma-$^{32}$P]ATP (Amersham, Arlington Heights, Ill.; specific activity=1445 Ci/mmol) was with the Bethesda Research Laboratories, Gaithersburg, Md. (BRL) kit according to manufacturer's instructions. Restriction enzyme digestions were with enzymes from BRL according to manufacturer's instructions.

Labeling the *S. typhimurium* 100kb plasmid with Tnmini-tet.

Strain Chi3000 containing pStLT100 was transformed with pNK861, which possesses Tnmini-tet (Way et al., *Gene* 32:369–79 (1984)). Tnmini-tet is essentially the Tet$^R$ gene of Tn10 within inverted repeats. pNK861 was excluded from the library of Amp$^R$ TetR Chi3000 (pStLT100, pNK861) by mobilizing in the incompatible plasmid pNK259 from Chi3000 (pNK259,F::Tn5) using F::Tn5. To select from Tnmini-tet insertions into the 100 kb plasmid, which is mobilizable by F, the Chi3000::Tnmini-tet (pNK259, F::Tn5) library was mated with *E. coli* HB101 selected for Tet$^R$, Kan$^R$ and Str$^R$. Potential Tnmini tet-labeled 100 kb plasmids in HB101 were mobilized back into *S. typhimurium* strain Chi3147 by selecting for Tet$^R$ and Nal$^R$. Several Nal$^R$, Tet$^R$, Kan$^S$ isolates which did not possess F::Tn5 were picked.

Tnmini-tet insertions in the 100 kb plasmid were transduced into each of the 100 kb plasmid-containing, wild-type *S. typhimurium* strains by phage P22 HT int-mediated transduction. Tet$^R$ transductants were screened for increased size of the 100 kb plasmid and alteration in the restriction enzyme profile from that of the parental plasmid.

An alternative method for isolating pStLT100::Tnmini-tet insertions was to obtain plasmid DNA from Chi3000 (pStLT100, pNK861) and to transform *E. coli* HB101 (pNK259), selecting for Tet$^R$ and Chl$^R$.

Curing *S. typhimurium* of the Tnmini-tet labeled 100 kb plasmid.

*S. typhimurium* strains with Tnmini-tet insertions in the 100 kb plasmid were subjected to two curing regimens—growth at 43° C. or growth in broth containing novobiocin. Tnmini-tet-labeled strains were passaged daily with low inocula (10$^3$–10$^4$ colony-forming units [CFU]) for each of the curing regimens. When cultures had reached stationary phase (OD$_{600}$ approximately 0.9), a portion was diluted and plated on L agar containing fusaric acid. Fusaric acid-resistant colonies were screened for Tet$^S$, and plasmid contents of fusaric acid-resistant, Tet$^S$ colonies were examined by using minilysate analysis. Cured derivatives were further examined by southern blot hybridization of minilysates and colony blot hybridization of bacterial cells with $^{32}$P-labeled pStSR100 to confirm curing and lack of a chromosomally integrated plasmid.

Mouse infections.

Seven to 10 week-old female BALB/c mice (Harlan Sprague/Dawley [Indianapolis] and Sasco [St. Louis]) were used for all animal infections. Older mice were used to obtain peritoneal macrophages. Normal mouse serum was obtained from male mice of various ages.

For p.o. inoculation, mice were food- and water-starved for 6 hours, then fed 50 microliters of 10% (wt/vol) sodium bicarbonate, followed by 20 microliters of bacteria suspended in buffered saline containing 0.1% (wt/vol) gelatin (BSG). Per oral inoculation was with a micropipet tip placed directly behind the incisors to avoid damage to the oral mucosa. Mice were fed food and water 30 minutes post-inoculation.

For i.p. inoculation and lateral tail vein intravenous (i.v.) inoculation, unfasted mice were injected with 0.1–0.2 ml of bacteria suspended in BSG.

Organs and tissues of infected mice were examined for presence of Salmonella as follows. Mice were killed by $CO_2$ asphyxiation. Spleens were aseptically removed and homogenized in 2.5 ml BSG in either an OMNI-mixer equipped with a microcup (Dupont, Wilmington, Del.) or a glass tissue homogenizer. Peyer's patches were removed from small intestines and washed twice by vortexing in 2 ml BSG. Rinsed Peyer's patches were homogenized in 2.5 ml BSG in either an OMNI-mixer or by vortexing in glass tubes containing glass beads. Mesenteric lymph nodes were homogenized in 2.5 ml BSG in glass tissue homogenizers. Dilutions of tissue and organ homogenates were plated on L agar plates containing appropriate antibiotics.

Statistical methods.

For comparison of CFU in tissues of mice infected with either wild-type or cured *S. typhimurium*, geometric means were determined and compared in a 1-tailed Student's t test for wild-type CFU being greater than cured CFR. For analysis of mixed infections, geometric means of ratios of wild-type to plasmid-cured CFU from individual mice were compared in a 1-tailed Student's t test for mean of $log_{10}$ of ratios greater than 0 (ratios greater than 1). Mouse $LD_{50}$ values were determined by the method of Reed and Muench (*Amer. J. Hyg.* 27:493–497 (1938)). Bacterial CFU in tissue culture and macrophage infections were compared by Student's t test of mean CFU/well in a 2-tailed test.

Presence of 100 kb plasmids in *S. typhimurium* strains.

All three strains of *S. typhimurium* studied possessed 100 kb plasmids (FIG. 3). In addition, Chi3339 possessed two other plasmids of 90 kb and 8 kb. The following three-part nomenclature system for 100 kb plasmids of the *S. typhimurium* strains was used in this study. To identify the serotype as *S. typhimurium*, the designation "St" was included. The strain designation ("LT" for LT2, "SR" for SR-11, and "SL" for SL1344) follows. A numerical designation finally identifies the plasmid as being wild-type (100) or a derivative (101 for a particular Tnmini-tet insertion, etc.). The wild-type plasmid of strain SR-11 therefore is pStSR100. Purified plasmid preparations were analyzed by restriction enzyme digestion, and identical profiles were obtained fro the 100 kb plasmids from all three strains with HindIII (FIG. 4) and EcoRI (data not shown). Restriction enzyme digestion of the 100 kb plasmid-cured SL1344, Chi3340, (FIG. 4, lane f) showed loss of the bands that correspond to the bands from pStLT100 (FIG. 4, lane b) and pStSR100 (FIG. 4, lane c), which were present in Chi3339 (lane e). Therefore, the 100 kb plasmids of each of the three *S. typhimurium* strains examined in these studies were very similar, if not identical.

Strain construction.

The transposon Tnmini-tet described by Way et al. (supra) was used to label 100 kb plasmids with a Tet-resistance marker. Tnmini-tet, a Tn10 derivative, does not possess the IS10R transposase gene within the inverted repeats hence the transposase gene is lost upon transposition from the donor plasmid, pNK861, and cannot subsequently mediate transposition or deletion of Tnmini-tet. Therefore, Tnmini-tet insertions are much more stable that those of the parent, Tn10.

A Tnmini-tet insertion into the 100 kb plasmid of strain Chi3000, resulting in pStLT101, allowed selection of derivatives cured of the 100 kb plasmid with a frequency of $10^{-6}$ to $10^{-7}$ cell$^{-1}$ generation$^{-1}$ following growth in novobiocin or growth at 43° C., yielding Chi3344. This same Tnmini-tet insertion was then transduced into Chi3339 and Chi3306 and was used to cure these strains of their 100 kb plasmids, yielding Chi3340 and Chi3337, respectively. Chi3340 retained the 90 kb and 8 kb plasmids (FIG. 3, lane h). Curing of 100 kb plasmids was confirmed by gel-electrophoresis of plasmid DNA from cleared lysates (FIG. 3) and hybridization of minilysates in Southern blots and lysed bacteria in colony blots with $^{32}$P-labeled pStSR100 (data not shown). Lack of hybridization in colony blots of the cured derivatives indicated that no chromosomally integrated plasmid was present. No plasmid-cured derivatives that possessed integrated plasmids were observed.

Tnmini-tet-labeled plasmids of Chi3000, pStLT101, and Chi3306, pStSR101, were reintroduced into cured derivatives by transformation, yielding Chi3347 and Chi3338, respectively. pStSR101 was transformed into Chi3340, yielding Chi3351 (Table 3, FIG., 3, lane i).

Mouse-virulence.

The p.o. $LD_{50}$s in BALB/c mice of each of the wild-type, cured, and retransformed derivatives were determined (Table 11). The p.o. $LD_{50}$s of the mouse-passaged Chi3306 and Chi3339 were $3 \times 10^5$ CFU and $6 \times 10^4$ CFU, respectively, and the p.o. $LD_{50}$ of Chi3000 was $>10^8$ CFU. The p.o. $LD_{50}$s of the respective cured derivatives were $>10^8$ CFU. Mice infected with Chi3337 and Chi3340 became sick, and occasional deaths were observed. The $LD_{50}$s of the 100 kb plasmid-retransformed derivatives were returned to those of the parental wild-type strains. This confirmed that the genetic lesion of cured derivatives was, in fact, loss of the 100 kb plasmid.

TABLE 11

Mouse $LD_{50}$ values[a] (CFU) for wild-type and 100 kb plasmid-cured *S. typhimurium*

| Strain | 100 kb plasmid | p.o. | i.p. |
| --- | --- | --- | --- |
| SR-11: | | | |
| χ3306 | + | $3 \times 10^5$ | <50 |
| χ3337 | − | $>10^8$ | <50[b] |
| χ3338 | + | $10^5$ | <50 |
| SL1344: | | | |
| χ3339 | + | $6 \times 10^4$ | <50 |
| χ3340 | − | $>6 \times 10^8$ | 400 |
| χ3351 | + | $<5 \times 10^4$ | <50 |
| LT2-Z: | | | |
| χ3000 | + | $>10^8$ | $2 \times 10^3$ |
| χ3344 | − | NT[c] | $2 \times 10^3$ |
| χ3347 | + | $>10^9$ | NT |

[a]Determined by the method of Reed an Meunsch (supra)

TABLE 11-continued

Mouse LD$_{50}$ values[a] (CFU) for wild-type and 100 kb plasmid-cured S. typhimurium

| Strain | 100 kb plasmid | p.o. | i.p. |
| --- | --- | --- | --- |

[b]Mean time to death for χ3337 (12.3 days) greater than that of χ3306 (7.0 dyas) (p < 0.001 Student's t test).
[c]NT — not tested I.p. LD$_{50}$s of wild-type and cured derivatives were not as different as were p.o. LD$_{50}$s (Table 11). The i.p. LD$_{50}$s of Chi3306 and Chi3339 were <50 CFU, with 100% mortality achieved with each of these inocula. The cured derivative of Chi3306, Chi3337, also killed most mice injected with less than 50 CFU. However, the mean time to death was greater for Chi3337 (12.3 days) relative to Chi3306 (7.0 days) (p<0.001, 1 tailed student's test). In contrast, the i.p. LD$_{50}$ of 100 kb plasmid-cured SL1344, Chi3340, was raised to 400 CFU from <50 CFU. Reintroduction of the Tnmini-tet-labeled 100 kb plasmid into Chi3340 restored the wild-type i.p. LD$_{50}$. The i.p. LD$_{50}$s for wild-type and cured LT2 strains were each approximately 2000 CFU.

Effects of plasmid exchange between strains SR-11 and LT2.

Strain LT2 was much less virulent than strain SR-11 by the p.o. route (Table 11). To determine if the 100 kb plasmids of these two strains had a role in this difference in virulence, the Tnmini-tet derivatives of each of the 100 kb plasmids were transformed into the heterologous cured strains. Mice infected p.o. with 10$^9$ CFU of strain SR-11 possessing either pStLT101 or pStSR101 died by 7 days post-inoculation, while strain LT2 was avirulent (p.o. inoculum 10$^9$ CFU) with either plasmid. Therefore, the avirulence of strain LT2 was not due to defects in its 100 kb plasmid. This result, in addition to that obtained by introducing the SR-11 plasmid, pStSR101, into strain SL1344 yielding virulent Chi3351 (Table 11), demonstrated that the 100 kb plasmids of these three strains were functionally equivalent.

Pathogenesis after p.o. inoculation.

The more distinct differences in virulence between wild-type and cured derivatives by the p.o. route versus the i.p. route raised the possibility that the 100 kb plasmid was involved in virulence in the gut instead of during later stages of invasive disease. To examine this possibility, mice were infected p.o., with either wild-type SR-11, Chi3306, or 100 kb plasmid-cured SR-11, Chi3337, and Peyer's patches and spleens were examined for S. typhimurium at various times post-infection. The composite results of three experiments are presented in FIG. 5. At 3 hours post-infection, very few S. typhimurium were detected in Peyer's patches (<100 CFU). This was not the result of inefficient passage of inocula from the oral cavity to the intestines as essentially 100% of inocula were recovered from the gut, primarily large intestinal contents, within 2 hours post-inoculation. Furthermore, CFU in the small intestinal contents were equal between wild-type and cured SR-11 up to 3 days post-inoculation. At 1 and 2 days post-inoculation, CFU in Peyer's patches gradually increased to 10$^3$ to 10$^4$ CFU, and CFU in spleens remained low. At 3 days post-inoculation, Peyer's patches and spleens possessed significantly more wild-type Chi3306 than cured Chi3337. The difference in CFU in Peyer's patches was not consistently observed in different experiments and, as the data for other time points indicate, was temporary. However, CFU in spleens remained significantly different with Chi3306 outnumbering Chi3337 in increasing amounts until mice infected with Chi3306 died by 8 days post-inoculation. Chi3337 in spleens reached levels on the order of 10$^4$ CFU and remained detectable in spleens as long as 25 days post-inoculation. Thus, the primary difference in pathogenesis after p.o. inoculation between wild-type and virulence plasmid-cured S. typhimurium SR-11 was in the numbers of S. typhimurium reaching and/or multiplying in spleens.

To more precisely compare the relative virulences of wild-type and plasmid-cured SR-11, mixed infection experiments with Tet$^R$, wild-type SR-11, Chi3456, and NalR, plasmid-cured SR-11, Chi3337, were done. Ratios of wild-type CFU to plasmid-cured CFU were determined for each mouse. In addition, ratios of CFU were determined for mesenteric lymph nodes, which are intermediate in the invasive process from Peyer's patches to spleens. Large ranges in CFU and ratios between individual mice were observed, necessitating analysis of geometric means of ratios. Composite results of three experiments are presented in FIG. 6. As observed for the experiments with mice infected with either wild-type of plasmid-cured S. typhimurium (FIG. 5), no significant differences in CFU in Peyer's patches or spleens were detectable in mice with mixed infections until 3 days post-inoculation when wild-type to cured ratios in Peyer's patches, mesenteric lymph nodes, and spleens were 11:1, 200:1, and 79:1, respectively. At 4 days post-inoculation, only the ratio for spleens was significantly greater than 1.0 (ratio= 160:1), while Peyer's patches and mesenteric lymph nodes had ratios of 1.5:1 and 13:1, respectively. Again, as observed in mice with separate infections, CFU in Peyer's patches were approximately equal for wild-type and cured SR-11 after the transient differences noted at 3 days post-inoculation. At 5 days post-inoculation, mesenteric lymph nodes and spleens possessed ratios of 200:1 and 1600:1, respectively; the Peyer's patch ratio was 1.1:1. At 7 days post-inoculation, a single mouse survived with Peyer's patch, mesenteric lymph node, and spleen ratios of 2.1:1, 290:1, and 210:1, respectively. The greatest differences in CFU in the various organs were in spleen and mesenteric lymph nodes relative to Peyer's patches. At 3, 4, and 5 days post-inoculation, spleen ratios were significantly greater than Peyer's patch ratios, and at 3 and 5 days post-inoculation mesenteric lymph node ratios were significantly greater than Peyer's patch ratios (FIG. 6).

The pathogenesis of wild-type SL1344, Chi3339, and 100 kb plasmid-cured SL1344, Chi3340, was investigated in mice infected p.o. Results of two experiments are presented in FIG. 7. At 3 days post-inoculation, no significant differences in CFU in Peyer's patched, mesenteric lymph nodes, or spleens were observed between wild-type and cured SL1344. At 7 to 8 days post-inoculation, significantly greater numbers of wild-type Chi3339 than cured Chi3340 were detected in all three organs. Greater differences were observed in mesenteric lymph nodes and spleens than in Peyer's patches. Furthermore, in one of the experiments, the difference in CFU in Peyer's patches was not significant. Thus, infection of mesenteric lymph nodes and spleens represented the major consistent difference in pathogenicities between wild-type and 100 kb plasmid-cured SL1344. By 14 days post-inoculation, all mice infected with wild-type Chi3339 had died, while mice infected with cured Chi3340 had infection of Peyer's patches and spleens of 2×10$^3$ CFU and 6.3×10$^3$ CFU, respectively. At 31 days post-inoculation, Peyer's patches and spleens of mice infected with Chi3340 possessed 400 CFU and 320 CFU, respectively. Thus, 100 kb plasmid-cured SL1344 survived in Peyer's patches and spleens for extended periods of time after p.o. inoculation.

Infection of spleens after i.v. inoculation.

The results described above indicated that the 100 kb plasmid was primarily involved in invasiveness from Peyer's patches to mesenteric lymph nodes and spleens after p.o. inoculation, instead of being involved in infection of Peyer's patches or earlier events. To examine growth of *S. typhimurium* in spleens, mice were inoculated i.v., with mixtures of wild-type SR-11, Chi3456, and plasmid cured SR-11, Chi3337, and spleens were monitored for CFU (Table 12). When mice were inoculated i.v., with $10^5$ CFU of Chi3456 and Chi3337, the strains were equally cleared to spleens 1 hour post-inoculation. Thus, presence of the 100 kb plasmid did not affect clearance from the blood. Other mice were inoculated i.v., with $1 \times 10^3$ to $4 \times 10^3$ CFU of mixtures of

TABLE 12

Infection of spleens after i.v. inoculation of mice[a]

| | Time post-inoculation | | |
|---|---|---|---|
| | 1 h[b] | 4 d[c] | 6–7 d[c] |
| CFU χ3456[d] | $1.9 \times 10^5$ | $4.6 \times 10^4$ | $2.7 \times 10^6$ |
| CFU χ3337[d] | $1.4 \times 10^5$ | $2.5 \times 10^4$ | $2.3 \times 10^{5e}$ |
| Ratio (χ3456:χ3337)[f] | 1.3:1 | 1.8:1 | 11.5:1 (P < 0.0025) |
| Ratio ± SD[g] | 0.11 ± 0.25 | 0.26 ± 0.38 | 1.06 ± 0.39 |

[a]Mice were inoculated i.v. with equal mixtures of wild-type χ3456 and 100 kb plasmid-cured χ3337. n = 3 to 5 mice.
[b]Inoculum = $5 \times 10^5$ CFU each of χ3456 and χ3337?
[c]Inoculum = $1 \times 10^4$ to $4 \times 10^4$ CFU each of χ3456 and χ3337 (equal inocula were given with each experiment)
[d]Geometric mean of CFU from spleens
[e]At 6 days post-inoculation, mice infected with $2 \times 10^3$ CFU of χ3337 alone possessed spleen levels of $2.3 \times 10^5$ CFU of χ3337
[f]Geometric mean of ratio χ3456:χ3337 (P value in 1-tailed Student's t test for ratio > 1:1)
[g]Mean of $\log_{10}$ of ratios ± standard deviation used for statistical analysis Chi3456 and Chi3337. No significant differences in CFU in spleens were detected at 4 days post-inoculation (Table 12). However, at 6 to 7 days post-inoculation, ratios of wild-type to cured *S. typhimurium* recovered from spleens were 11.5:1. At this time, mean levels in spleens of Chi3456 and Chi3337 were $2.7 \times 10^6$ and $2.3 \times 10^5$ CFU, respectively. Thus, plasmid-cured SR-11 survived and replicated in spleens for extended periods of time after i.v., inoculation. The wild-type to cured ratio for SR-11 in spleens of 11.5:1 at 1 week post-i.v., inoculation contrasted sharply with the ratios of 1600:1 and 210:1 obtained 5 and 7 days after p.o. inoculation. The lower ratio obtained with mixed i.v., inoculation was not due to synergy between Chi3456 and Chi3337 because at 6 days post-inoculation, mice infected with $2 \times 10^3$ CFU of Chi3337 alone or Chi3337 mixed with equal amounts of Chi3456 attained mean spleen levels of $2.3 \times 10^5$ CFU for Chi3337 (Table 12).

Plasmid-cured *S. typhimurium* were able to multiply in Peyer's patches and reached mesenteric lymph nodes and spleens after p.o. inoculation (FIGS. 5, 6, 7). However, differences in the abilities of wild-type versus plasmid-cured *S. typhimurium* to invade to mesenteric lymph nodes and spleens were consistently found. It was also determined that wild-type *S. typhimurium* was much more efficient at infecting spleens after p.o. inoculation of mice (wild-type to cured ratios of 1600:1; FIG. 6). However, even cured derivatives reached spleen levels as high as $10^4$ CFU and remained detectable in spleens for as long as 31 days post-inoculation (FIG. 5). After p.o. inoculation with mixtures of wild-type and cured SR-11, significantly higher ratios of wild-type to cured SR-11 were found in spleens and mesenteric lymph nodes as compared with Peyer's patches (FIG. 6).

The i.p. $LD_{50}$s of plasmid-cured SR-11 and SL1344 were <50 CFU and 400 CFU, respectively, indicating that 100 kb plasmid-cured *S. typhimurium* retained significant virulence by this route of inoculation (Table 11). It is important to note that neither cured strain hybridized with $^{32}$P-labeled virulence plasmid, so the presence of a chromosomally integrated copy of the plasmid which could contribute to virulence was ruled out. The abilities of wild-type and cured strains to infect spleens after i.v., inoculation was investigated and significant differences in CFU in spleens one week after i.v., inoculation with mixtures of wild-type and cured *S. typhimurium* (mean wild-type to cured ratios of 7.5:1 and 20:1) were found. The differences in spleen CFU after i.v. inoculation were not as large as those obtained 5 to 7 days after p.o. inoculation (1600:1- and 210:1-fold). These experiments again demonstrated that plasmid-cured *S. typhimurium* could reach high levels and multiply in spleens and that the greatest effects of the 100 kb plasmid on pathogenesis are after p.o. inoculation. We hypothesize that 100 kb plasmid-cured *S. typhimurium* retains virulence by the i.p. route because the bacteria rapidly multiply extracellularly and are not efficiently phagocytosed in the peritoneal cavity; hence an overwhelming infection develops before mice can check the infection by clearing bacteria to macrophgages. When administered by the p.o. route, all or most of the invading bacteria are presumed to be intracellular upon reaching the mesenteric lymph nodes.

Example 4

This Example illustrates the construction of delta-cya, delta-crp, and delta-Cya delta-crp derivatives of *S. choleraesuis*, the virulence properties of the mutants after peroral (p.o.) inoculation, and the immunogenicity of these derivatives.

Bacterial strains.

The *S. choleraesuis* strains used in this Example are listed in Table 13. Bacterial strains were grown at 37° C. in L broth and on L agar (Lennox, 1955; Luria and TABLE 13
Salmonella strains.

| Strain No. | Relevant genotype | Source |
|---|---|---|
| *S. typhimurium* strains | | |
| χ3000 | wild type LT2-Z | Obtained from C. Turnbough (Zinder and Lederberg. 1952) |
| χ3042 | wild type SL1344 | Hoiseth and Stocker, 1981 Gulig and Curtiss, 1987 |
| PP1002 | cya::Tn10 trpB223 | Postma et al., 1986; Curtiss and Kelly, 1987 |
| PP1037 | crp773::Tn10 trpB223 | Postma et al., 1986; Curtiss and Kelly, 1987 |
| χ3339 | wild type SL1344 | mouse-passaged χ3042 Gulig and Curtiss, 1987 |
| χ3385 | galE496 hsdL6 hsdSA29 | restriction$^-$, modification$^+$ |

TABLE 13-continued
Salmonella strains.

| Strain No. | Relevant genotype | Source |
|---|---|---|
| χ3477 | Δ[galE-uvrB]-1005 hsdL6 hsdSA29 | derived from AS68 of T. Palva; Gulig and Curtiss, 1988 Gulig and Curtiss, 1987 |
| χ3485 | cya::Tn10 galE496 hsdL6 hsdSA29 | P22HT int(PP1002) → χ3385 |
| χ3486T | cya::Tn10 galE496 hsdL6 hsdSA29 | χ3485 lysogenized with P1 clr clm |
| χ3524 | Δ[galE-uvrB]-1005 crp773::Tn10 hsdL6 hsdSA29 | P22HT int(PP1037) → χ3477 |
| χ3604 | cya::Tn10 | P22HT int(PP1002) → χ3339 |
| χ3605 | crp773::Tn10 | P22HT int(PP1037) → χ3339 |
| χ3615 | Δcya-12 | Fusaric acid$^r$, tetracycline$^s$ derivative of χ3604 |
| χ3623 | Δcrp-11 | Fusaric acid$^r$, tetracycline$^s$ derivative of χ3605 |
| χ3656 | galE hsdL6 hsdLT hsdSA hsdSB gsdA1 shf-4::Tn10 | Nakayama et al., 1988 |
| χ3670 | (pSD110) galE496 hsdL6 hsdSA29 | χ3385 transformed with pSD110 |
| χ3711 | Δcya-12 zid-62::Tn10 | P22HT int(χ3738) → χ3615 |
| χ3738 | zid-62::Tn10 | P22HT int(TT2104) → χ3000 Sanderson and Roth, 1983 |
| χ3741 | zhb::Tn10 | P22HT int(DU8802) → χ3000 Sanderson and Roth, 1983 |
| χ3757 | Δcya-12 zid-62::Tn10 galE496 hsdL6 hsdSA29 | P22HT int(χ3711) → χ3385 |
| χ3773 | Δcrp-11 zhb::Tn10 | P22HT int(3741) → χ3623 |
| χ3819 | Δcrp-11 zhb::Tn10 galE496 hsdL6 hsdSA29 | P22HT int(χ3773) → χ3385 |
| *S. choleraesuis* strains | | |
| χ3246 | 5451-84 swine isolate wild type | William Fales, University of Missouri, Columbia |
| χ3492 | cya::Tn10 | P1 clr clm(χ3486T) → χ3246 |
| χ3751 | crp773::Tn10 | P1L4(χ3524) → χ3246 |
| χ3752 | Δcrp-19 | Fusaric acid$^r$, tetracycline$^s$ derivative of χ3751 |
| χ3753 | Δcya-24 | Fusaric acid$^r$, tetracycline$^s$ derivative of χ3492 |
| χ3755 | (pSD110) Δcrp-19 | P1L4(χ3670) → χ3752 |
| χ3759 | (pSD110) Δcrp-19 Δcya-12 zid-62::Tn10 | P1L4(χχ3757) → χ3755 |
| χ3775 | (pSD110) Δcrp-19 Δcya-12 | Fusaric acid$^r$, tetracycline$^s$ derivative of χ3759 |
| χ3781 | Δcrp-19 Δcya-12 | χ3775 cured of pSD110 |
| χ3820 | Δcrp-11 zhb::Tn10 | P1L4(χ3819) → χ3246 |
| χ3858 | Δcya-12 zid-62::Tn10 | P1L4(χ3757) → χ3246 |
| χ3859 | Δcya-12 | Fusaric acid$^r$, tetracycline$^s$ derivative of χ3858 |
| χ3860 | Δcrp-11 | Fusaric acid$^r$, tetracycline$^s$ derivative of χ3820 |
| χ3903 | wild type | χ3246 cured of 50 kb virulence plasmid |

Burrous, 1957), Penassay agar (Difco antibiotic media #3+ 1.5% BBL agar, Becton Dickinson Microbiology Systems, Cockeysville, Md.) and MacConkey Base agar (Difco Laboratories) with 1% final concentration of an appropriate carbohydrate. Media were supplemented with MgSO$_4$ (10 mM), CaCl$_2$ (5 mM), tetracycline (12.5 micrograms/ml) and ampicillin (100 micrograms/ml) when required. Synthetic media were minimal liquid and minimal agar supplemented with nutrients at optimal levels as previously described (Curtiss et al., 1968, Bacteriol. Rev. 32:320)). Buffered saline with gelatinn (BSG) was used as a diluent (Curtiss, 1965, J. Bacteriol. 89:28).

The pertinent refernces in Table 13 are the following.
Zinder and Lederbert (1952, J. Bacteriol. 64:679).
Hoiseth and Stocker (1981, Nature 291:238).
Gulig and Curtiss (1987, Infect. Immun. 55:2891).
Postma et al. (1986, J. Bacteriol. 168:1107.
Curtiss and Kelly (1987, Infect. Immun. 55:3035)
Gulig and Curtiss (1988, Infect. Immun. 56:3262).

Genetic manipulations.

Transductions were performed with bacteriophages P1L4 or P22 HT int with standard methods and media, as described in Curtiss (1981, Manual of Methods for General Bacteriology, American Society for Microbiology, Gerhardt et al., eds, p.243), Schmeiger (1972, Mol. Gen. Genet. 119:75), and Davis et al. (1980, A Manual for Genetic Engineering: Advanced Bacterial Genetics, Cold Spring Harbor Laboratory, Cold Spring Harbor, N.Y.). The methods and media described by Maloy and Nunn (1981, J. Bacteriol. 145:1110) were used for fusaric acid selection for deletion mutations in strains with Tn10 insertions. Transformations were performed by the method of Dagert and Ehrlich (1979, Gene 6:23). The plasmid, pSD110, which carries the crp and Amp$^r$ genes from *E. coli*, which was described in Schroeder and Dobrogosz (1986, J. Bacteriol. 167:616), was generously provided by C. Schroeder. Curing of the virulence plasmid was facilitated by use of pYA2028 which has the Inc/Par region of the virulence plasmid cloned into the high copy number plasmid pUC18, as described below.

Animal infectivity studies.

Female BALB/c mice (Harlan Sprague-Hawley, Indianapolis, IN) were used for all infectivity and immunization studies. Seven-week-old mice were held for one week in a quarantined room prior to being used in experiments. Animals were housed in Nalgene filter-covered cages with raised wire floors. Food and water were given ad libitum. The animal room was maintained at 22° C. to 23° C. with 12 h of illumination daily.

Virulence of *S. choleraesuis* strains was determined after p.o. inoculation. Bacteria for inoculation in mice were grown overnight as static cultures at 37° C. in L broth. All cultures were diluted 1:20 into prewarmed L broth and aerated at 37° C. for approximately 5 h to an optical density at 600 nm of about 0.8 to 1.0. The cells were concentrated 50-fold by centrifugation at 8,000×g for 10 min at room temperature, followed by suspension in BSG. Dilutions were plated on MacConkey agar with 1% maltose to verify the Cya or Crp phenotype and to enumerate cells.

Prior to p.o. inoculations, mice were deprived of food and water for 4 h before infection. They were then given 30 microliters of 10% (wt/vol) sodium bicarbonate 5–10 min before being fed a 20 microliter aliquot of *S. choleraesuis* cells suspended in BSG. Food and water were returned 30 min after the inoculation. Data on morbidity and mortality of mice were collected daily.

Evaluation of protective immunity.

Groups of five mice/cage were perorally immunized with various doses of avirulent mutants and then challenged 30 days later with various doses of the wild-type, virulent parent, Chi3246. Morbidity and mortality conditions were observed for at least 60 days.

Construction of *S. choleraesuis* strains with cya and crp mutations.

The highly virulent strain Chi3246 was used as the parent in the construction of all the vaccine strains used in these studies (the peroral $LD_{50}$ value for Chi3246 is presented in Table 14, infra.)

The strains which were constructed which were derived from Chi3246 are shown in Table 13. Also shown in Table 13 are the relevant genotypes of the strains, and a description of the method by which the strain was derived, utilizing the methods for transposon insertion via transduction, transposon deletion, as well as the selection methods described in Example 1, with the modifications described below.

Introduction of cya::Tn10, crp::Tn10, delta-cya- 12, and delta-crp-11 from the *S. typhimurium* strains PP1002, PP1037, Chi3615, and Chi3623, respectively (see Table 13), into *S. choleraesuis* strain Chi3246 was facilitated by P1L4 transduction (via intermediate *S. typhimurium* hosts Chi3385 and Chi3477) and transformation with pSD110. *S. choleraesuis* strain Chi3246 which is P22HTint resistant is, however, P1L4 immune. Thus, P1L4 or P1 clr clm immune bacteriophage can adsorb to and inject DNA into the cells of all *S. choleraesuis* strains used in this example, but are unable to replicate their DNA in these bacterial cells.

Since delta-Cya-12 zid-62::Tn10, delta-crp-11 zhb::Tn10, crp773::Tn10 and cya::Tn10 mutations are in *S. typhimurium* strains Chi 3711, Chi3773, PP1037 and PP1002, respectively (see Table 13), it was necessary to move the mutations from the smooth-LPS *S. typhimurium* background into an intermediate Salmonella host in which both P22HTint and P1L4 could be propagated. The bacteriophages P22HTint and P1L4 are specific for strains with smooth and rough LPS coats, respectively. The hosts, Chi3385 and Chi3477, are restriction-deficient, modification-proficient galE *S. typhimurium* strains. Growth of Chi3385 and Chi3477 in media with low concentrations of galactose permits synthesis of UDP-galactose, resulting in normal levels of LPS side chains; these conditions are essential for attachment and infection by P22HTint. Growth of Chi3385 and Chi3477 in media containing glucose and lacking galactose permits synthesis of a rough or incomplete LPS, and enables the adsorption and replication of P1L4 or P1 clr clm in these rough strains. By these means, the *S. choleraesuis* strains Chi3492, Chi3751, Chi3755, Chi3759, Chi3820, and Chi3858 were constructed. In the latter two strains, the Tn10 linked to the delta-cya or delta-crp mutation was eliminated by selection for fusaric acid resistance to yield Chi3860 and Chi3659, respectively.

TABLE 14

Mortality of BALB/c mice 30 days after peroral inoculation with wild-type *Salmonella choleraesuis* and its derivatives[a]

| Strain number | Genotype | Inoculating dose (CFU) | Survival live/total |
|---|---|---|---|
| χ3246 | Wild-type | $1.9 \times 10^5$ | 0/5 |
| | | $8.0 \times 10^4$ | 4/5 |
| χ3492 | cya::Tn10 | $7.8 \times 10^8$ | 5/5 |
| | | $7.8 \times 10^6$ | 5/5 |
| | | $7.8 \times 10^4$ | 5/5 |
| | | $1.5 \times 10^9$ | 5/5 |
| | | $1.5 \times 10^8$ | 5/5 |
| | | $1.5 \times 10^7$ | 5/5 |
| χ3751 | crp::Tn10 | $1.3 \times 10^9$ | 3/5 |
| | | $1.3 \times 10^7$ | 5/5 |
| | | $1.3 \times 10^5$ | 5/5 |
| | | $1.3 \times 10^9$ | 4/5 |
| | | $1.3 \times 10^8$ | 4/5 |
| | | $1.3 \times 10^7$ | 5/5 |
| χ3752 | Δcrp-19 | $1.3 \times 10^9$ | 3/5 |
| | | $1.3 \times 10^7$ | 5/5 |
| | | $1.3 \times 10^5$ | 5/5 |
| X3753 | Δcya-24 | $1.0 \times 10^9$ | 5/5 |
| | | $1.0 \times 10^7$ | 5/5 |
| | | $1.0 \times 10^5$ | 5/5 |
| | | $9.6 \times 10^8$ | 5/5 |
| | | $9.6 \times 10^7$ | 5/5 |
| | | $9.6 \times 10^6$ | 5/5 |
| χ3820 | Δcrp-11 zhb::Tn10 | $5.6 \times 10^8$ | 15/15 |

[a]Following a 4-hour food and water fast, eight-week-old female mice were inoculated with the indicated strains and doses. Daily morbidity and mortality data were observed for 30 days post-immunization.

In order to determine whether different deletion mutations generated by the excision of Tn10 from cya or crp exhibit different levels of virulence and/or immunogenicity, two different deletion mutants of cya and crp were constructed in *S. choleraesuis* Chi3246. Two deletions were isolated in, and transduced from *S. typhimurium* as described above, and are represented by *S. choleraesuis* strains Chi3859 (delta-cya-12) and Chi3860 (delta-crp-11). The other two deletion mutations wre isolated by excision of Tn10 inserted into the *S. choleraesuis* cya and crp genes in Chi3492 and Chi3751, respectively, using selection for fusaric acid resistance to yield Chi3752 (delta-crp-19) and Chi3753 (delta-cya- 24), respectively.

Construction of a *S. choleraesuis* strain with deletion mutations in both cya and crp genes was facilitated by using pSD110, which encodes the *E. coli* gene $crp^+$ gene. pSD110 was thus transduced into Chi3752 (Table 13), and this was followed by trasducing in the delta-Cya12 mutation, which is closely linked to zid- 62::Tn10 by selection for tetracycline resistance and screening for inability to ferment maltose, which is indicative of the introduction of the cya mutation. Following selection of Chi3759 for fusaric acid resistance to eliminate Tn10, pSD110 was cured by growth at 43° C. to yield Chi3781 (See Table 13). The serotype of all constructs was confirmed by agglutination with Salmonella group $C_1$ O-antigen antisera.

Phenotypic analysis of cya and crp mutants.

The cya mutants (Chi3492, Chi3753, Chi3859), the crp mutants (Chi3751, Chi3752, Chi3820) and the cya crp mutant (Chi3781) were subjected to phenotypic analysis. These strains failed to ferment maltose, mannitol, sorbitol, and melibiose, and slowly fermented galactose. The phenotypes were as expected based on known requirement for cAMP, and for CRP for catabolic activities. The requirements for cAMP, and for CRP for regulation of gene expression are described in the following refernces. Perlman and Pastan (1969, Biochem. Biophys. Res. Comm. 37:151); Pastan and Perlman (1970, Science 169:339); Schwartz and Beckwith (1970, the lac Operon, Zipser and Beckwith, eds., Cold spring Harbor Laboratory, N.Y.); Pastan and Adhya (1976, Bacteriol. Rev. 40:527); and Scholte and Postma (1980, *J. Bacteriol.* 141:757).

Construction of virulence plasmid-cured derivatives of *S. choleraesuis* and of its delta-cya and/or delta-crp strains.

We have discovered that the Inc/Par region of the virulence plasmid of *S. typhimurium*, which encodes incompatibility and partition functions, hybridizes to and exhibits incompatibility with the virulence plasmid of *S. choleraesuis*. Based upon this finding, pYA2028, which contains the Inc/Par region of the virulence plasmid of *S. typhimurium*, high copy number pUC vector was used to facilitate in the curing of the the virulence plasmid from *S. choleraesuis*. Introduction of pYA2028 into *S. cholerasuis* was accomplished using essentially either the transformation methods described in Dagert and Ehrlich (1979, supra.) or the electroporation methods of Feidler and Worth (1988, Anal. Biochem. 170:38). Transformants were selected for, and maintained by, the inclusion of ampicillin in the medium. After several generations of growth, the virulence plasmid is lost due to incompatibility exclusion. Growth of the cured *S. choleraesuis* strain for subsequent cycles in media without ampicillin leads to a rapid loss of pYA2028. The resulting cells lack both the virulence plasmid and pYA2028. Chi3903 represents a virulence plasmid cured derivative of the wild-type *S. choleraesuis* strain Chi3246. As described in Example 3, loss of the virulence plasmid reduces the ability of Salmonella to reach and/or colonize deep tissues such as the liver and spleen, but is without effect in terms of colonization of the intestinal tract and the GALT. Elimination of the virulence plasmid thus reduces virulence without diminishing immunogenicity. Removal of the virulent plasmid from the double cya crp mutants would follow the same procedure.

Virulence of cya and crp mutant strains in mice.

In order to study the virulence of the *S. choleraesuis* strains listed in Table 13, groups of mice were orally inoculated with 100-fold varying doses of each strain. The results are shown in Table 14. The p.o. $LD_{50}$ of the parental wild-type strain (Chi3246), which was ~1× $10^5$ CFU, was determined by the method of Reed and Muench (1938). This $LD_{50}$ is much lower than those of the respective cya and crp strains.

The data in Table 14 show that the mutant strains are avirulent at at least 6,000 times the $LD_{50}$ of the parental wild-type strain, Chi3246. Mice orally infected with $10^9$ CFU of Chi3751 (crp::Tn10) and Chi3752 (delta-crp) became scruffy, lethargic, inappetent, and some died. However, all mice infected with the same dose of Chi3492 (cya::Tn10) and Chi3753 (delta-cya24) became slightly ill, recovered, and survived the dose. This dose represents 12,500 times the $LD_{50}$ of the wild-type parent strain. It is therefore evident that the cya::Tn10 and delta-cya mutants are more avirulent than the crp::Tn10 and delta-crp mutants. This result is somewhat surprising since the opposite has been found with *S. typhimurium* delta-cya and delta-crp infections in mice.

The results also showed that there were no obvious difference in the health of the animals inoculated with delta-crp-19 compared to delta-crp-11 strains, and delta-cya-12 as compared to delta-cya-24 strains.

Virulence of the strains with both delta-cya and delta-crp may also be established using the above described procedure.

Immunogenicity of cya and crp mutant strains.

The ability of the different *S. choleraesuis* mutants to induce immunity to subsequent oral challenge with the wild-type virulent parent, Chi3246, was examined. Mice were inoculated p.o. with the *S. choleraesuis* delta-cya and delta-crp strains shown in Table 15, at the indicated doses. Thirty days after immunization with the attenuated strains, mice were challenged p.o. with Chi3246. Morbidity and mortality were observed daily for 30 days post-challenge. The results in Table 15 reveal the apparent differences in the degrees of immunogenicity of the different strains. Mice immunized with $10^7$, $10^8$, or $10^9$ CFU of the somewhat more virulent strains with mutations in crp exhibited better health and a higher rate of survival after oral challenge with Chi3246 than did mice immunized with the less virulent cya mutant strains. Thus, animals immunized with $10^9$ CFU of the cya mutants

TABLE 15

Effectiveness of immunization with attenuated *Salmonella choleraesuis* vaccine strains in BALB/c mice to challenge with wild-type virulent *S. choleraesuis*[a]

| Strain number | Genotype | Immunizing dose (cfu) | Wild-type Challenge (cfu) | Survival live/total |
|---|---|---|---|---|
| χ3492 | cya::Tn10 | $7.8 \times 10^8$ | $1.1 \times 10^9$ | 2/5 |
| | | $7.8 \times 10^6$ | $1.1 \times 10^9$ | 0/5 |
| | | $7.8 \times 10^4$ | $1.1 \times 10^9$ | 0/5 |
| | | $1.5 \times 10^9$ | $2.4 \times 10^9$ | 2/5 |
| | | $1.5 \times 10^8$ | $2.4 \times 10^9$ | 1/5 |
| | | $1.5 \times 10^7$ | $2.4 \times 10^9$ | 0/5 |
| χ3751 | crp::Tn10 | $1.3 \times 10^9$ | $1.1 \times 10^9$ | 3/3 |
| | | $1.3 \times 10^7$ | $1.1 \times 10^9$ | 2/5 |
| | | $1.3 \times 10^5$ | $1.1 \times 10^9$ | 0/5 |
| | | $1.3 \times 10^9$ | $2.4 \times 10^9$ | 4/4 |
| | | $1.3 \times 10^8$ | $2.4 \times 10^9$ | 3/4 |
| | | $1.3 \times 10^7$ | $2.4 \times 10^9$ | 2/5 |
| χ3752 | Δcrp-19 | $1.3 \times 10^9$ | $1.1 \times 10^9$ | 3/3 |
| | | $1.3 \times 10^7$ | $1.1 \times 10^9$ | 4/5 |
| | | $1.3 \times 10^5$ | $1.1 \times 10^9$ | 0/5 |
| χ3753 | Δcya-24 | $1.0 \times 10^9$ | $1.1 \times 10^9$ | 2/5 |
| | | $1.0 \times 10^7$ | $1.1 \times 10^9$ | 0/5 |
| | | $1.0 \times 10^5$ | $1.1 \times 10^9$ | 0/5 |
| | | $9.6 \times 10^8$ | $2.4 \times 10^9$ | 2/5 |
| | | $9.6 \times 10^7$ | $2.4 \times 10^9$ | 2/5 |
| | | $9.6 \times 10^6$ | $2.4 \times 10^9$ | 2/5 |
| χ3820 | Δcrp-11 zhb::10 | $5.6 \times 10^8$ | $1.0 \times 10^9$ | |

[a]Following a 4-hour food and water fast, eight-week-old female mice were inoculated with the indicated strains and doses. Thirty days after immunization with the attenuated strains, mice were challenged with a peroral dose of wild-type virulent χ3246. Daily morbidity and mortality data were observed for an additional 30 days post-challenge.

had a rate of survival below 50% whereas 100% of the mice immunized with $10^9$ cells of the crp strain survived challenge; in fact, those immunized with $10^7$ or $10^8$ cells of the crp strain survived challenge with $10^9$ cells of the wild-type strain.

The immunogenicity of cya crp mutants of *S. choleraesuis* is determined by immunizing the mice with a high, but sublethal dose (8×$10^8$ CFU) of the attenuated strains. Thirty days later, survivors are challenged with Chi3246 at $10^1$, $10^2$, and $10^3$ times the $LD_{50}$ value of Chi3246 Morbidity and mortality conditions are observed as described above.

Construction of asd cya crp mutants of *S. choleraesuis*

Salmonella vaccine strains can serve as carriers to deliver a foreign antigen to the GALT of an animal host by introduction of a gene encoding the antigen into the vaccine strains. Nakayama et al., (1988, Bio/Tech 6:693) described a unique system where an Asd$^+$ expression-cloning vector was constructed for the purpose of high-level stable expression of foreign antigen genes in delta-cya delta-crp delta-asd S. typhimurium. The avirulent properties of the delta-cya delta-crp mutations have been consistently proven with doses administered to mice at approximately 1000 times the LD$_{50}$ of the wild-type parent in all Salmonella species previously tested. These avirulent strains have also stimulated a protective immune response in the immunized animals as demonstrated by challenge with approximately 1000 times the wild-type parent. Repeated animal experiments have confirmed that the S. choleraesuis delta-Cya and delta-crp strains are avirulent and immunogenic in mice. It can be deduced from earlier results obtained from studies on avirulence and immunogenicity that a S. choleraesuis construct with delta-cya and delta-crp mutations would be avirulent and immunogenic. The addition of the delta-asd mutation to the S. choleraesuis delta-cya delta-crp Chi3781 is facilitated by bacteriophage P22 HT int transduction to a restriction-deficient, modification-proficient intermediate S. typhimurium with subsequent propagation of bacteriophage p1L4 on the intermediate S. typhimurium host and final transduction of delta-asd into the S. choleraesuis vaccine strain.

S. typhimurium Chi3656 is grown in L broth containing 5 mM CaCl$_2$, and infected with P1L4 to propagate a high titer lysate. The P1L4(Chi3656) lysate is then used to transduce S. choleraesuis delta-cya delta-crp Chi3781; transductants are screened for by tetracycline resistance. A portion of the tetracycline-resistant transductants are screened for the Asd$^-$ phenotype. As a final step, selection on fusaric acid media is performed to identify a tetracycline-sensitive derivative of the S. choleraesuis delta-cya delta-crp delta-asd strain. Additional characterization of the final construct is completed by verifying the markers and presence of a complete LPS coat, and by the non-acquirement of additional auxotrophic phenotypes.

Deposits of Strains

The following listed materials are on deposit under the terms of the Budapest Treaty, with the American Type Culture Collection, 12301 Parklawn Drive, Rockville, Md. The accession number indicated was assigned after successful viability testing, and the requisite fees were paid. Access to said cultures will be available during pendency of the patent application to one determined by the Commissioner to be entitled thereto under 37 CFR 1.14 and 35 USC 122. All restriction on availability of said cultures to the public will be irrevocably removed upon the granting of a patent based upon the application. Moreover, the designated deposits will be maintained for a period of thirty (30) years from the date of deposit, or for five (5) years after the last request for the deposit; or for the enforceable life of the U.S. patent, whichever is longer. Should a culture become nonviable or be inadvertently destroyed, or, in the case of plasmid-containing strains, loose its plasmid, it will be replaced with a viable culture(s) of the same taxonomic description. The deposited materials mentioned herein are intended for convenience only, and are not required to practice the present invention in view of the description herein, and in addition, these materials are incorporated herein by reference.

| Strain | Deposit Date | ATCC No. |
| --- | --- | --- |
| Chi4062 | July 15, 1987 | 53647 |
| Chi4064 | July 15, 1987 | 53648 |
| Chi3781 delta-crp-19 delta-cya-12 | March 29, 1989 | 67923 |
| Chi3903 (wild-type, 50kb plasmid-cured) | March 29, 1989 | 53885 |
| Chi3246 (wild-type) | March 29, 1989 | 67922 |

Commercial Utility

The strains provided herein are directly and indirectly suitable for the production of commercial vaccines to prevent diseases caused by S. choleraesuis, and other enteric bacteria with which antibodies to S. choleraesuis cross react. These strains are also useful as carrier microorganisms for the production of expression products encoded on recombinant genes in the bacterial cells.

I claim:

1. A vaccine for immunization of an individual comprising a live avirulent S. choleraesuis obtained from a pathogenic strain of S. choleraesuis, said avirulent S. choleraesuis being made avirulent by an inactivating mutation in a cya gene and an inactivating mutation in a crp gene.

2. A vaccine for the immunization of an individual according to claim 1, wherein said avirulent S. choleraesuis expresses in the individual a recombinant gene derived from an agent which is pathogenic to said individual, to produce an antigen which induces an immune response in said individual against said pathogen.

3. A vaccine according to claim 2, wherein said individual is a vertebrate.

4. A method for stimulating the immune system to respond to an immunogenic antigen of S. choleraesuis comprising administering to an individual a live avirulent S. choleraesuis obtained from a pathogenic strain of S. choleraesuis, said avirulent S. choleraesuis being made avirulent by an inactivating mutation in a cya gene and an inactivating mutation in a crp gene.

5. A method for stimulating the immune system to respond to an immunogenic antigen of a pathogen comprising administering to an individual a live avirulent S. choleraesuis obtained from a pathogenic strain of S. choleraesuis, said avirulent S. choleraesuis being made avirulent by an inactivating mutation in a cya gene and an inactivating mutation in a crp gene and which expresses in said individual a recombinant gene encoding the immunogenic antigen, to produce an antigen capable of inducing an immune response in said individual against said pathogen.

6. A method according to claim 5, wherein said individual is a vertebrate.

* * * * *